(12) United States Patent
Brik et al.

(10) Patent No.: US 9,175,053 B2
(45) Date of Patent: Nov. 3, 2015

(54) CHEMICAL PREPARATION OF UBIQUITIN THIOESTERS AND MODIFICATIONS THEREOF

(75) Inventors: Ashraf Brik, Be'er-Sheva (IL); Mahmood Haj-Yahya, Taybe-Meshulash (IL); Ajish Kumar, Kochi (IN); Leslie Erlich, Hertzilya (IL); Liat Spasser, Hertzilya (IL)

(73) Assignee: BEN-GURION UNIVERSITY OF THE NEGEV RESEARCH AND DEVELOPMENT AUTHORITY, Beer-Sheva (IL)

( * ) Notice: Subject to any disclaimer, the term of this patent is extended or adjusted under 35 U.S.C. 154(b) by 0 days.

(21) Appl. No.: 13/578,014
(22) PCT Filed: Feb. 9, 2011
(86) PCT No.: PCT/IL2011/000138
§ 371 (c)(1),
(2), (4) Date: Oct. 31, 2012
(87) PCT Pub. No.: WO2011/098999
PCT Pub. Date: Aug. 18, 2011

(65) Prior Publication Data
US 2013/0041132 A1 Feb. 14, 2013

Related U.S. Application Data
(60) Provisional application No. 61/302,559, filed on Feb. 9, 2010.

(51) Int. Cl.
C07K 14/47 (2006.01)
C07K 14/00 (2006.01)
(52) U.S. Cl.
CPC .............. *C07K 14/47* (2013.01); *C07K 14/00* (2013.01)
(58) Field of Classification Search
None
See application file for complete search history.

(56) References Cited

U.S. PATENT DOCUMENTS

| 4,786,684 | A | * | 11/1988 | Glass | .......................... 525/54.1 |
| 6,977,292 | B2 | | 12/2005 | Botti et al. | |
| 2011/0184148 | A1 | * | 7/2011 | Hojo et al. | .................... 530/334 |

FOREIGN PATENT DOCUMENTS

| WO | 03106615 A2 | 12/2003 | |
| WO | 2009032133 A2 | 3/2009 | |
| WO | 2009032181 A2 | 3/2009 | |
| WO | WO 2012/005691 | * 6/2010 | ............ C07C 323/60 |

OTHER PUBLICATIONS

Ruggles et al., 2007, A Viable Synthesis of N-Methyl Cysteine, Peptide Science, 90(1): 61-68.*
McGinty et al., published Oct. 2, 2009, Structure-Activity Analysis of Semisynthetic Nucleosomes: Mechanistic Insights into the Stimulation of Dot1L by Ubiquitylated Histone H2B, ACS Chemical Biology, 4(11): 958-968.*
Kumar et al., published Sep. 24, 2009, Highly Efficient and Chemoselective Peptide Ubiquitylation, Angew Chem Int Ed, 48: 8090-8094.*
Hojo et al., 2007, N-Alkyl cysteine-assisted thioesterfication of peptides, Tetrahedron Letters, 48: 25-28.*
Bang et al., 2006, Kinetically Controlled Ligation for the Convergent Chemical Synthesis of Proteins, Angew Chem Int Ed, 45: 3985-3988.*
Bang et al., 2005, Total Chemical Synthesis and X-ray Crystal Structure of a Protein Diasteromer: [D-Glu35]Ubiquitin, Angew Chem Int Ed, 44: 3852-3856.*
Yang et al., 2010, Synthesis of K48-linked diubiquitin using dual native chemical ligation at lysine, Chem. Commun. 46: 7199-7201.*
Haj-Yahya et al., 2010 Protecting Group Variations of d-Mercaptolysine Useful in Chemical Ubiquitylation, Peptide Science, 94(4): 504-510.*
Kent, 2009, Total chemical synthesis of proteins, Chem. Soc. Rev., 38: 338-351.*
Bang et al: "Total Chemical Synthesis and X-ray Crystal Structure of a Protein Diastereomer: [D-Gin 35]Ubiquitin", Angewandte Chemie International Edition, vol. 44, No. 25,Jun. 20, 2005, pp. 3852-3856.
Kumar et al: "Highly Efficient and Chemoselective Peptide Ubiquitylation", Angewandte Chemie International Edition, vol. 48, No. 43, Oct. 12, 2009, pp. 8090-8094.
Ollivier et al: "Fmoc Solid-Phase Synthesis of Peptide Thioesters Using an Intramolecular N , S -Acyl Shift", Organic Letters, vol. 7, No. 13, Jun. 1, 2005, pp. 2647-2650.
Kawakami T et al: "The use of a cysteinyl prolyl ester (CPE) autoactivating unit in peptide ligation reactions", Tetrahedron, Elsevier Science Publishers, Amsterdam, NL, vol. 65, No. 19, May 9, 2009, pp. 3871-3877.
Haj-Yahya et al: "Protecting group variations of [delta]mercaptolysine useful in chemical ubiquitylation", Biopolymers, vol. 94, No. 4, Jun. 3, 2010 , pp. 504-510.
Pasunooti etal: "Synthesis of 4-mercapto-1-lysine derivatives: Potential building blocks for sequential native chemical ligation", Bioorganic & Medicinal Chemistry Letters, Pergamon, Elsevier Science, GB, vol. 19, No. 22, Nov. 15, 2009, pp. 6268-6271.
Erlich et al: "N-Methylcysteine-mediated total chemical synthesis of ubiquitin thioester", Organic & Biomolecular Chemistry, vol. 8, No. 10, Mar. 11, 2010 , p. 2392.
Kumar et al: "Total Chemical Synthesis of Di-ubiquitin Chains", Angewandte Chemie International Edition, vol. 49, No. 48, Sep. 2, 2010, Nov. 22, 2010, pp. 9126-9131.
Hojo et al: "N-Aikyl cysteine-assisted thioesterification of peptides", Tetrahedron Letters, Elsevier, Amsterdam, NL, vol. 48, No. 1, Nov. 30, 2006, pp. 25-28.
Supplementary European Search Report issued in corresponding European Patent Application No. EP11741976.2 dated Jun. 25, 2013.

* cited by examiner

*Primary Examiner* — Amber D Steele
(74) *Attorney, Agent, or Firm* — Browdy and Neimark, PLLC

(57) ABSTRACT

The present invention discloses latent thioester functionalities attached to the C-terminus of a first polypeptide, or a first fragment thereof having a Cys residue at its N-terminus, and a process using this functionality for the preparation of polypeptide thioesters, in particular of ubiquitin thioesters, this process comprising preparing a polypeptide or a fragment thereof, being attached to a latent thioester functionality, which can then be ligated with a second polypeptide fragment, followed by selective activation of the latent thioester functionality group, to provide the requested polypeptide thioester. There are also provided the polypeptides obtained by this method, specific unnatural amino acids useful to be incorporated within the polypeptide thioesters, and kits for preparing them.

2 Claims, No Drawings

CHEMICAL PREPARATION OF UBIQUITIN THIOESTERS AND MODIFICATIONS THEREOF

The topic of peptide thioesters synthesis has captured the interest of many research groups motivated by the importance of thioester peptides in native chemical ligation and in protein synthesis.

Current methods to prepare peptide thioesters employ Boc- or Fmoc-Solid phase peptide synthesis (SPPS) approach in combination with methods relying on the use of safety catch linkers, N-acyl urea based chemistry and N—S acyl transfer devices employing latent thioester functionalities. One example of a N—S acyl transfer method combined with Boc- or Fmoc-SPPS is the reaction of N-alkylated Cys at the C-terminal peptide with 3-mercaptopropionic acid (MPA) to generate the desired peptide thioester (for example, F. Nagaike et al., Org. Lett., 2006, 8, 4465).

However, these methods are good for peptide fragments up to 30-40 amino acids and are difficult, and sometimes even impossible, to apply for peptides having more than 70 amino acids.

Ubiquitin (Ub) is a highly conserved globular 76-residue eukaryotic protein found in the cytoplasm and nucleus of cells. Ubiquitin exists both as a monomer and as isopeptide-linked polymers known as poly-ubiquitin chains.

The in-vivo process of ubiquitylation serves as a recognition marker for degradation (in the case of polyubiquitylation) and to regulate different biochemical processes (in monoubiquitylation). Three distinct enzymes, known as the E1-E3 system, collaborate to achieve a site-specific ubiquitylation of the lysine residue(s) in the target protein. The activation of α-COOH of ubiquitin is achieved in an ATP dependent manner using the E1 enzyme, which forms a thioester with the carboxyl group of Gly76. This step activates ubiquitin and triggers a nucleophilic attack by the conjugating enzyme E2. The latter transiently carries the activated ubiquitin, also as a thioester intermediate, and with the assistance of the E3 ligase transfers ubiquitin to a specific lysine residue of the protein substrate.

It can be seen that ubiquitin thioesters (UbSRs) are key intermediates in the ubiquitylation of proteins, and it is of great interest to be able to synthesize & modify them and study their properties.

However, since ubiquitin is made of 76 amino acids, applying the Boc- or Fmoc-SPPS-based methods described above to prepare thioester derivatives thereof, is very challenging and would require alternative means to achieve such a goal.

Indeed, the current methods to prepare Ub-SRs are relying on either the use of the enzymatic machinery E1-E2 or on expressed protein technology. However, these approaches are limited mainly to natural amino acids modification, thereby inhibiting chemical manipulation of ubiquitin. The chemical synthesis of protein thioester, wherein unnatural amino acids could be incorporated into the sequence, remains a synthetic challenge.

Kent and coworkers have applied native chemical ligation (NCL) for the synthetic preparation of peptides in general (U.S. Pat. No. 7,030,217) and Ub peptides in particular (Bang et al, *Angew. Chem. Int. Ed. Eng.*, 44, 3852-3856, 2005) and have later reported a "kinetically controlled ligation" strategy for preparing protein thioesters (for example, D. Bang et al., Angew. Chem. Int. Ed., 2006, 45, 3985). This approach exploits the different reactivities of aryl and alkyl thioesters as well as the differences in the bulkiness of the C-terminal residue of the thioester peptides for a convergent protein synthesis. However, the process disclosed by Kent et al. could lead to an undesirable outcome when the C-terminal residue of the thioester peptides is intrinsically reactive in peptide ligation, as is the case in ubiquitin where the C-terminal residue is Gly.

Therefore, there is a continuing need to develop new processes for the chemical synthesis of Ub-SRs and analogs thereof.

The inventors have now developed a thioester "switchable device", also termed latent thioester functionality, that is attached to a solid support and can then be the first building block in "growing" or elongating a peptide, such as ubiquitin, on the solid support to obtain the desired protein. This can be done either in one step or by the use of native chemical ligation of smaller fragments of this peptide, as long as the C-terminal fragment of the peptide shall be the one attached to this thioester "switchable device". Once the required protein has been obtained, the "switchable device" can be turned into a thioester by reacting it with an external thiol under acidic conditions, preferably at a pH lower than 4, most preferably at a pH of about 2.

This is an important advantage of the latent thioester functionality, since in contrast to common linkers used in NCL, it will not be removed neither upon removal from the solid support, nor under ligation conditions, which are at a pH of about 7 and higher, and needs an activating step of lowering the pH to below 4 for it to be removed. In other words, the LTF group can be "switched off" at a specific point in time, by lowering the pH, as detailed herein.

Thus, according to one aspect of the invention there is provided a process of chemically preparing polypeptide thioesters, this process comprising:
 a) Attaching a Latent Thioester Functionality (LTF) to a solid support;
 b) Chemically synthesizing a polypeptide or a fragment thereof on this solid support, followed by removal from the solid support, to obtain an N-terminal unprotected polypeptide or an N-terminal unprotected fragment thereof, attached to a latent Thioester Functionality on its C-terminal;
 c) If a polypeptide fragment is obtained in step b:
  i. Chemically synthesizing in one or more steps, a complimentary fragment to the fragment obtained in step b, whereas the complimentary fragment is prepared as a thioester;
  ii. Reacting the thioester of the complimentary fragment with the fragment attached to the latent Thioester Functionality obtained in step b, by native chemical ligation (NCL) to obtain a polypeptide attached to the latent Thioester Functionality;
 d) Reacting the polypeptide being attached to the latent Thioester Functionality with an external thiol under acidic conditions to obtain the polypeptide thioester.

The term "polypeptide" as used herein refers to a sequential chain of amino acids linked together via peptide bonds and encompasses an amino acid chain of any length. If a single polypeptide can function as a unit, the terms "polypeptide" and "protein" may be used interchangeably, however, in general, the term does include peptides, proteins, fusion proteins, oligopeptides, cyclic peptides, and polypeptide derivatives.

The term "polypeptide fragment" is used interchangeably with the term "polypeptide segment" and refers to a peptide or polypeptide, having either a completely native amide backbone or an unnatural backbone or a mixture thereof, ranging in size from 2 to 1000 amino acid residues, preferably from 2-99 amino acid residues, more preferably from 10-60 amino acid residues, and most preferably from 20-40 amino acid residues. Each peptide fragment can comprise native amide bonds or any of the known unnatural peptide backbones or a mixture thereof. Each peptide fragment can be prepared by any known synthetic methods, including solution synthesis, stepwise solid phase synthesis, segment condensation, and convergent condensation.

The term "unnatural amino acid" refers to any amino acid, modified amino acid, and/or amino acid analogue, that is not one of the 20 common naturally occurring amino acids or the rare naturally occurring amino acids e.g., selenocysteine or pyrrolysine.

As used herein, the term "thioester", interchangeably used with the term "thioloester", refers to a moiety represented by —COSR, often connected to a peptide.

The term "peptide thioester" or "polypeptide in its thioester form" may be represented as "peptide-α-COSR". The R group in this case may be any number of groups, including 1-15 C functionalized alkyl, straight or branched, 1-15 C aromatic structures, 1-4 amino acids or derivatives thereof, preferably wherein the R group is selected such that the peptide-α-COSR is an activated thioester.

The term "Chemically synthesizing" refers to the fact that the obtaining of the polypeptide, and in particular obtaining the polypeptide thioester, is not conducted enzymatically or by gene expression, neither in vivo nor in vitro.

The term "Latent thioester Functionality", used interchangeably with the term "thioester device" or "switchable device", describes any functionality that is able to undergo a S→N acyl transfer and withstand the removal from the solid support, as well as the ligation conditions. This functionality therefore serves to introduce into the polypeptide structure, a precursor to the thioester group to be unmasked at the last stages of the reaction, only upon an activation step, upon providing acidic conditions.

Preferably, the "Latent thioester Functionality" has the general structure outlined in Formula I:

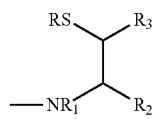

Formula I

Wherein:

R is either hydrogen or a thiol protecting group;

The compound of formula I would attach to the growing peptide through the Nitrogen attached to $R_1$, whereas:

$R_1$ is selected from the group consisting of: hydrogen, C1-C3 alkyl, C1-C3 alkyl-COOH, C1-C3 alkyl-CONH$_2$, C1-C3 alkylene-CONH$_2$, C1-C3 alkylene-CO$_2$H, SO$_2$-alkyl; SO$_2$-alkyl-CONH$_2$, benzyl and derivatives thereof, alkyl-nitrile and alkyl-halogens. Additional or specific examples include: iodomethyl, nitromethyl, derivatives of benzyl like o-nitro-benzyl, p-nitro benzyl;

Preferably, $R_1$ is selected from hydrogen, C1-C3 alkyl, C1-C3 alkyl-CONH$_2$, SO$_2$—C1-C3 alkyl-CONH$_2$, C1-C3 alkyl-COOH.

More preferably, $R_1$ is selected from hydrogen, methyl, ethyl, C1-CONH$_2$ and C1-COOH.

$R_2$ and $R_3$ are selected from the group consisting of: hydrogen, CO$_2$H, CH$_2$CO$_2$H, —CH$_2$OH, CONH$_2$, CH$_2$—CONH$_2$ and CH$_2$NH$_2$, as well as N-protected derivatives thereof.

Preferably, $R_2$ is selected from hydrogen, CONH$_2$ and N-protected derivatives thereof. This includes for example CO—N(prolyne amino acid).

According to one specific embodiment of the invention, $R_3$ is hydrogen.

Furthermore, at least one of $R_1$ and $R_2$ should contain a linking group CONH$_2$ or N-protected derivatives thereof, that would be attached to the solid support.

As noted herein, optionally, the thiol side chain (R) in this latent thioester functionality is protected to avoid intramolecular N—S acyl transfer in the cleavage step from the SPPS resin.

Examples of thiol-protecting groups include, but are not limited to, triphenylmethyl (trityl, Trt), acetamidomethyl (Acm), benzamidomethyl, 1-ethoxyethyl, acetyl, benzoyl, substituted and unsubstituted benzyl groups and the like.

Preferably, the thiol-protecting group is a substituted benzyl group, whereas the phenyl group is substituted by an alkoxy, such as methoxy, ethoxy and the like or by a nitro group.

Most preferably, the thiol protecting group is a photo-labile thiol group, such as 2-nitrobenzyl.

Upon completion of the ligation reaction, the thiol-protecting group, if present, is removed (for example by UV), followed by treatment of the fully unprotected polypeptide with a thiol, such as MPA, under acidic conditions (i.e. pH<4), to afford the target polypeptide-thioester.

According to some preferred embodiments of the invention, exemplified below, the Latent Thioester Functionality (LTF) is selected from:

i. R=hydrogen or 2-nitrobenzyl; $R_1$=hydrogen or methyl; $R_2$=CONH$_2$; $R_3$=hydrogen;
ii. R=hydrogen or 2-nitrobenzyl; $R_1$=hydrogen or methyl; $R_2$=CO—N-pyrroline; $R_3$=hydrogen;
iii. R=hydrogen or 2-nitrobenzyl; $R_1$=methyl, ethyl or benzyl; $R_2$=hydrogen; $R_3$=hydrogen;
iv. R=hydrogen or 2-nitrobenzyl; $R_1$=C1 alkyl-CONH$_2$ or C1 alkyl-COOH; $R_2$=hydrogen; $R_3$=hydrogen.

Most preferably, the Latent Thioester Functionality (LTF) is N-methyl cysteine. In this case, $R_1$ is methyl; $R_2$ is CONH$_2$ and $R_3$ is hydrogen. The inventors have shown that the N-methyl cysteine reacts as expected, both when R is hydrogen and both when it is 2-nitrobenzyl.

Examples of some protected latent thioester functionality attached to peptides, and their reactions to obtain the polypeptide-thioesters, are shown in scheme below:

Scheme 1A

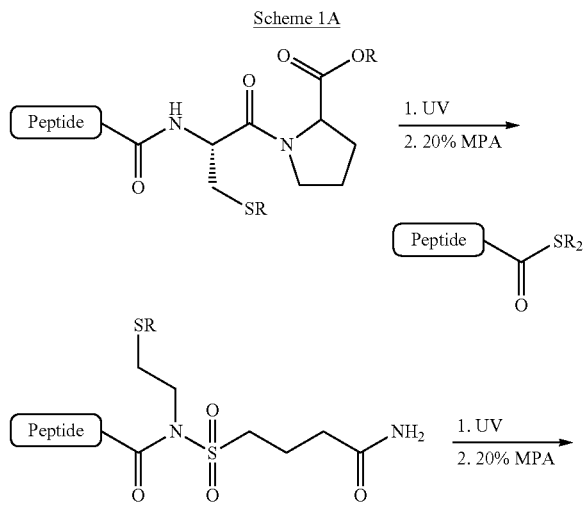

-continued

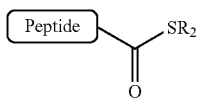

$R_2$ = alkyl or aryl group
R = 2-nitrobenzyl

Scheme 1B is similar, referring in particular to cases when the "peptide" in scheme 1A is ubiquitin, and when no protection exists on the LTF's thiol group (R in formula I being hydrogen).

Scheme 1B

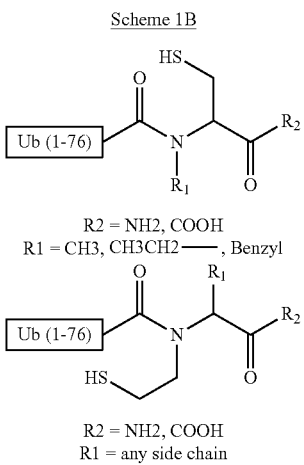

R2 = NH2, COOH
R1 = CH3, CH3CH2——, Benzyl

R2 = NH2, COOH
R1 = any side chain

The term "solid support" is used interchangeably with the term "solid Phase" and refers to a material having a surface and which is substantially insoluble when exposed to organic or aqueous solutions used for coupling, deprotecting, and cleavage reactions.

Examples of solid support materials include glass, polymers and resins, including polyacrylamide, PEG, polystyrene PEG-A, PEG-polystyrene, macroporous, POROS™, cellulose, reconstituted cellulose (e.g. Perloza), nitrocellulose, nylon membranes, controlled-pore glass beads, acrylamide gels, polystyrene, activated dextran, agarose, polyethylene, functionalized plastics, glass, silicon, aluminum, steel, iron, copper, nickel and gold. Such materials may be in the form of a plate, sheet, petri dish, beads, pellets, disks, or other convenient forms.

Some of the examples and embodiments described herein refer to resins, which are a type of solid support, and one of ordinary skill in the art would understand that such examples are not meant to be limited to resins, but to solid phases in general.

As used herein, the phrase "peptide attached to a solid support via a latent thioester functionality" refers to a solid phase-bound peptide, comprising at least one peptide fragment bound to a solid phase via a functionality that is able to undergo a S→N acyl transfer and withstand the ligation conditions (pH of about 7 and higher), be stable to stepwise solid phase chemistries, be able to be covalently linked in unprotected form to the solid phase, and be cleavable without damaging the assembled polypeptide.

According to a preferred embodiment of the invention, the latent thioester functionality is attached to the solid support via an amide bond.

Most important, in order to obtain the thioester as the final product, the latent thioester functionality must remain attached to the polypeptide, or to the fragment thereof, during the removal of each fragment from the solid support, as well as throughout ligation and be selectively removed therefrom, only upon activation, such as providing acidic conditions, and reaction with an external thiol at the last stages of the reaction.

In particular, the term "ligation conditions" refers to 6 M Gn.HCl, 200 mM phosphate buffer, pH of about 7 (from about 7 to about 8) for a period ranging from 4 hours to 48 hours.

The term "removal from the solid support" refers to cleavage of the polypeptide or peptide fragment containing the latent thioester functionality, from the solid support. It is essential that during this stage, the entire peptide-LTF is cleaved from the solid support, and that the LTF remains indeed attached to the peptide or the fragment thereof.

The following conditions can be used for cleavage of the peptide-LTF to release the assembled polypeptide from the solid phase using TFA/TIS/$H_2O$ (95:2.5:2.5).

The polypeptide fragment obtained by SPPS is an unprotected polypeptide or fragment. Namely, it does not contain protection groups on the side chains of the amino acids.

In particular, it should be noted that the latent thioester functionality is attached to the C-terminal fragment of the grown peptide, and that the N-terminal of the polypeptide remains unprotected, this being an advantage of Native Chemical Ligation.

The term "N-terminal" is interchangeably used with "N-terminus" or "N-terminus amino acid" and refers to mean, as used herein, the amino acid whose carboxyl group participates in the formation of the peptide bond, but which has a free amino group. In a linear peptide, the N terminus is conventionally written to the left.

The term "C-terminal" is interchangeably used with "N-terminus" or "C-terminus amino acid" and refers to mean, as used herein, the amino acid whose amino group participates in the formation of the peptide bond, but which still has a free carboxyl group. In a linear peptide, the C-terminus is conventionally written to the right.

If the polypeptide or peptide attached to the latent thioester functionality, is a fragment of the complete desired polypeptide to be made into a thioester form, then a second, complimentary fragment must be prepared separately from the first fragment.

The term "complimentary fragment" as used herein refers to a peptide fragment that, when attached to the fragment obtained in step b, forms the complete sequence of the desired polypeptide.

The complimentary fragment can be made in one or more steps, as required.

The preparation of the peptide fragments is preferably conducted by SPPS, according to techniques known to those skilled in the art.

Preferably, the SPPS is an Fmoc synthesis, but Boc synthesis can also be used.

The term "Native chemical ligation" as used herein refers to chemoselective reactions involving ligation of a first unprotected amino acid, peptide or polypeptide and a second unprotected amino acid, peptide or polypeptide resulting in the formation of an amide bond having a backbone structure indistinguishable from that of a peptide or polypeptide occurring in nature or via recombinant expression. The Native Chemical Ligation is conducted according to techniques known to those skilled in the art.

Although several ligation reactions can be conducted to obtain the final peptide from fragments comprising it, either on the main backbone of the polypeptide, or via side chains thereof, preferably, the ligation reaction is between a Cysteine amino acid on the C-terminal of the polypeptide and a thioester on the N-terminal the polypeptide. Therefore, the fragments are preferably prepared such that the N-terminal the polypeptide would be in a thioester form, and that the C-terminal of the polypeptide would contain a Cys terminal amino acid, or an equivalent thereof.

The cys amino acid, which is used to effect the NCL, can be turned into Ala amino acid by desulfurization, either after the ligation step, or after obtaining the thioester peptide, in order to revert to the native polypeptide structure after ligation.

Thus, after removal of fragment 2 from the solid support, the polypeptide C-terminal fragment 2, having a Cys amino acid on its N-terminal side and a "latent thioester functionality" on its C-terminal side, would have the structure of general Formula II:

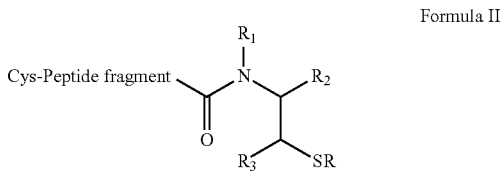

Formula II wherein R, $R_1$, $R_2$ and $R_3$ are as defined hereinabove.

Once this fragment is ligated with fragment 1 (the N-terminal peptide fragment-thioester) the total polypeptide (for example, ubiquitin or Ub analog) is obtained, being still linked to the latent thioester functionality.

In another embodiment, if the full polypeptide is attached to the latent thioester functionality, a similar structure would be obtained, wherein instead of the Cys-peptide fragment, there would be a Peptide attached to the latent thioester functionality.

Following the ligation, if necessary, the obtained polypeptide attached to the latent thioester functionality, can be reacted with an external thiol under acidic conditions to activate the removal of the LTF and to obtain the requested polypeptide thioester.

It can be seen that the "latent thioester functionality" attached to the C-terminal side of a peptide or a fragment thereof (for example as depicted by Formula II) is independent and stable and can be kept as such until the moment when ligation and/or activation are required, the LTF group acting as a switchable device", there is now provided yet a new aspect of the invention.

Thus, according to this additional aspect of the invention, there is provided a latent thioester functionality (LTF) attached to the C-terminus of a first polypeptide, or to a first fragment thereof having a Cys residue at its N-terminus.

Preferably, the latent thioester functionality has the general Formula I:

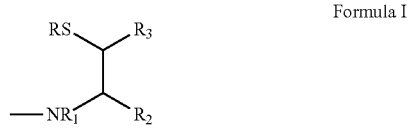

Formula I

Wherein:
R is either hydrogen or a thiol protecting group;
The thioester functionality being attached to the first Ub polypeptide fragment via the Nitrogen attached to $R_1$,
Further wherein $R_1$ is selected from the group consisting of: hydrogen, C1-C3 alkyl, C1-C3 alkyl-COOH, C1-C3 alkyl-CONH$_2$, C1-C3 alkylene-CONH$_2$, C1-C3 alkylene-CO$_2$H, SO$_2$-alkyl; SO$_2$-alkyl-CONH$_2$, benzyl and derivatives thereof, alkyl-nitrile and alkyl-halogens;

Yet further wherein $R_2$ and $R_3$ are independently selected from the group consisting of: hydrogen, CO$_2$H, CH$_2$CO$_2$H, —CH$_2$OH, CONH$_2$CH$_2$—CONH$_2$ and CH$_2$NH$_2$, as well as N-protected derivatives thereof, Such that at least one of $R_1$ and $R_2$ should contain a linking group CONH$_2$ or N-protected derivatives thereof.

Preferably, the latent Thioester Functionality (LTF) is a residue of N-methyl cysteine.

Given the importance of modifications in the peptide chain, the polypeptide contains at least one unnatural amino acid. Preferably, this unnatural amino acid is a 1,2 thioamine containing amino acid. More preferably, the 1,2 thioamine containing amino acid is a protected mercaptolysine. This compound was used for example in the preparation of tetra-Ub, as demonstrated in parallel patent application 11-069, as disclosed hereinabove (Ub3$_{k48}$-LTF).

According to one preferred embodiment, the peptide or peptide fragment to which the latent thioester functionality is attached is ubiquitin. However any other LTF-attached polypeptide combination is included within the scope of this invention.

The term "thiol" or "thiol compound" as used herein, represents a group of formula —SH. The term "external thiol" emphasizez that the thiol group comes from an external reagent, namely a reagent other than the polypeptide or fragments thereof.

Examples of thiol compounds include, but are not limited to, mercaptoaminomethane, 2-mercapto-1-aminoethane, 3-mercapto-1-aminopropane, 4-mercapto-1-aminobutane, 1,1,1-triamino-2-mercaptoethane, mercaptoacetic acid, 2-mercaptopropionic acid, 3-mercaptobutyric acid (MPA), 4-mercaptovaleric acid and 1,1,1-triamino-3-mercaptopropane.

Some other exemplary external thiols are shown in scheme 2 below:

Scheme 2

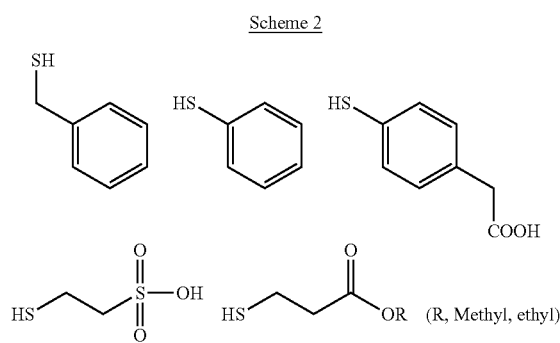

Preferably, the external thiol used for the final stage in the afore-mentioned process, is 3-mercaptopropionic acid (MPA).

The term "acidic conditions" refers to a pH substantially lower than 7, preferably a pH which is under 6, more preferably under 4. Most preferably, the necessary acidic pH for "switching off" the latent thioester functionality, is a pH from about 1 to about 2.

It should be noted that for "switching off" the latent thioester functionality, the acidic conditions can be provided in one step with the addition of the external thiol, for example when the thiol is an acid such as MPA. Alternatively, namely, when the external thiol is not an acid or is not acidic enough, the conditions should be modified by adjusting the pH to the required pH described herein.

As shown in the Experimental section which follows, the process described hereinabove was successfully applied for the long-sought chemical preparation of ubiquitin thioesters.

Thus, according to one aspect of the invention, there is provided a process for the preparation of ubiquitin thioesters, this process comprising:
- a) Attaching a Latent Thioester Functionality (LTF) to a solid support;
- b) Chemically synthesizing a ubiquitin monomer or a fragment thereof on this solid support, followed by removal from the solid support, to obtain an N-terminal unprotected ubiquitin monomer or an N-terminal unprotected ubiquitin fragment, attached to the latent Thioester Functionality on its C-terminal;
- c) If a ubiquitin fragment is obtained in step b:
  - i. Chemically synthesizing a second ubiquitin fragment to be complimentary to the ubiquitin fragment obtained in step b, whereas the second ubiquitin fragment is prepared as a thioester;
  - ii. Reacting the thioester of the second ubiquitin fragment with the ubiquitin fragment attached to the latent Thioester Functionality obtained in step b, by native chemical ligation (NCL) to obtain a ubiquitin monomer attached to the latent Thioester Functionality;
- d) Reacting the ubiquitin monomer being attached to the latent Thioester Functionality with an external thiol under acidic conditions to obtain the ubiquitin thioester.

As used herein, the term "ubiquitin" or Ub includes within its scope all known as well as unidentified eukaryotic Ub homologs of vertebrate or invertebrate origin. Examples of Ub polypeptides as referred to herein include the human Ub polypeptide that is encoded by the human Ub encoding nucleic acid sequence (GenBank Accession Numbers: U49869, X04803) as well as all equivalents.

For example, natural human Ub protein has the following sequence, containing the following 76 amino acids:

(SEQ ID NO: 1)
MQIFVKTLTGKTITLEVEPSDTIENVKAKIQDKEGIPPDQQRLIFAGKQ

LEDGRTLSDYNIQKESTLHLVLRLRGG.

Therefore, according to one preferred embodiment, the ubiquitin polypeptide is a natural ubiquitin polypeptide.

However, as used herein, the term "ubiquitin" (Ub) also includes modified ubiquitin polypeptides.

The term "modified Ub" as used herein refers to polypeptides containing one or more unnatural amino acids replacing one or more of the 76 native Ub amino acids.

For example, in the ensuing examples, an equivalent sequence to natural Ub was synthetically prepared, replacing the Met amino acid with a Leucine amino acid (namely to obtain the following sequence: LQIFVKTLTGKTITLEVE-PSDTIENVKAKIQDKEGIPPDQQRLIF-AGKQLEDGRTLSDYNIQ KESTLHLVLRLRGG) (SEQ ID NO:2), thereby avoiding oxidation of the Met. Similarly, another equivalent is obtained by replacing the Met with nurleucine (Nle). However, the invention also works with the original Met amino acid.

Additional examples to modified Ub include replacing Leu amino acids in positions 28 or 46 by a 1,2 thioamine containing amino acid, such as mercaptolysine derivatives (as shown in Example 7 below), or by introducing a labeled amino acid, or an amino acid linked to a specific reagent etc. Additional useful modifications can be envisioned by a person skilled in the art and are therefore included in the scope of this invention.

Thus, according to one preferred embodiment, the ubiquitin polypeptide is a modified ubiquitin polypeptide.

The ubiquitin according to the present invention includes both mono-ubiquitin and poly-ubiquitin. In other words, the ubiquitin may appear as having either one or several ubiquitin monomers.

The term "Ub monomer", used interchangeably with the term "Ub unit", as used herein, refers to a 76-amino acid sequence of ubiquitin, either natural or modified.

Furthermore, this term includes ubiquitin-like-modifiers (ULM), also termed "ubiquitin-like" or "Ubl" protein modifiers. This terms, as used herein, refers to the group of small proteins that are subject to conjugation machinery similar to that for ubiquitination. Examples of Ubl protein modifiers include NEDD8, ISG15, SUMO1, SUMO2, SUM03, APG12, APG8, URM1, Atg8, URM1, HUB1, FUB1, FAT10, UBL5, UFM1, MLP3A-LC3, ATG12, as well as other Ubl protein modifiers yet to be identified.

The process for preparing Ub thioesters, is disclosed in detail hereinabove as part of the general discussion on preparing polypeptide thioesters according to the present invention, whereas the terms "polypeptide" or "peptide" therein should be read to refer to ubiquitin polypeptides. All other terms are as described hereinabove.

While the process described herein can be conducted by "elongating" one long chain of the Ub monomer/unit on the solid support, to which the LTF is attached, this process is less desirable for the 76-amino acid-long ubiquitin, having lower yields and is generally less convenient, since any modification in this long chain requires a complete synthesis of the entire 76-amino acid chain.... Therefore, although complete synthesis of Ub thioesters has been demonstrated in the Examples below, using native chemical ligation (NCL) of shorter fragments of the Ub monomer is a preferred embodiment of the present invention.

Since one preferable way of conducting NCL is based on a reaction of a thioester fragment with a Cys amino acid on the second peptide fragment, and since the natural Ub sequence has no Cys amino acids, NCL of ubiquitin fragments is preferably conducted in the positions containing Ala amino acids (namely positions 28 and 46), by chemically introducing one or more Cys amino acids into one or more of those positions, whereas at some stage after the ligation, the Cys is turned back into native Ala by desulfurization.

For example, the process described herein can be performed wherein the ubiquitin monomer is prepared of two ubiquitin segments by NCL, such that the fragment attached to the LTF is: AGKQLEDGRTLSDYNIQKESTLHLVLRL-RGG (Ub46-76) (SEQ ID NO:3) and the second fragment being in its thioester form is LQIFVKTLTGKTITLEVEPS-DTIENVKAKIQDKEGIPPDQQRLIF (Ub1-45) (SEQ ID NO:4), whereas the $A_{46}$ amino acid is temporarily replaced by Cysteine.

Another option for preparing the Ub of two ubiquitin segments is wherein the fragment attached to the LTF is: AKIQDKEGIPPDQQRLIF-AGKQLEDGRTLSDYNIQKESTLHLVLRLRGG (Ub28-76) (SEQ ID NO:5) and the second fragment, being in its thioester form, is LQIFVKTLTGKTITLEVEPSDTIENVK (Ub1-27) (SEQ ID NO:6), whereas the $A_{28}$ amino acid is temporarily replaced by Cysteine.

The ubiquitin can further be ligated from three fragments. In this case, the process described herein needs to be somewhat modified as follows:

First, both (Ub46-76) and (Ub28-45) (AKIQDKEGIPP-DQQRLIF (SEQ ID NO:7) and AGKQLEDGRTLSDY-NIQKESTLHLVLRLRGG (SEQ ID NO:3), respectively) fragments are separately prepared on solid supports, wherein both the $A_{46}$ and the $A_{28}$ amino acids are temporarily replaced by Cysteine, each being attached to an LTF group, as described above according to the embodiments of the present invention, and are removed from these supports.

Then, Ub(1-27) (LQIFVKTLTGKTITLEVEPSD-TIENVK) (SEQ ID NO:6) fragment is separately prepared on a solid surface, removed and turned into a thioester to obtain Ub(1-27)-SR.

NCL OF the two fragments Ub(1-27)-SR and the modified C28-Ub(29-45)-LTF is conducted to obtain the Ub(1-45), still attached to the LTF group. Following activation under acidic conditions and a reaction with an external thiol, the Ub1-45 thioester is obtained.

Finally, NCL OF C46-Ub(47-76)-LTF and (UB 1-45)-SR follows, as conducted in the ligation of the two Ub fragments.

As shown in Example 5, the inventors have shown that the synthetic ubiquitin thioester obtained by this method has a similar behavior in peptide ubiquitylation as the ubiquitin thioester obtained via gene expression.

The newly developed process is advantageous in allowing higher flexibility in the chemical manipulation of ubiquitin thioesters in a wide variety of ubiquitylated peptides and proteins for structural and biochemical analysis and for the synthesis of ubiquitin chains.

Indeed, the successful application of this method in the preparation of poly-Ub chains is described in a patent application being co-filed on the same date as the instant application, having the reference number 11-069, claiming the same priority (provisional application No. 61/302,359) and entitled "Chemical Preparation Of Polyubiquitin Chains", which is incorporated by reference as if fully set forth herein.

It should be noted that although the examples and description provided herein are based on the ligation and corresponding fragments as described hereinabove, the ligation can be conducted between other ligation sites, and the fragments would be chosen according to the requirements of this other ligation process, as known to a person skilled in the art, without changing the scope of the invention.

One specific embodiment of the invention for obtaining Ub-SR is provided in Scheme 3 below and in Examples 3 and 4. This process is based on the synthesis of the Ub monomer from two fragments, which include peptide 1 Ub(46-76) and peptide 2 Ub(1-45)-SR, wherein $Ala_{46}$ is mutated temporarily to Cys to facilitate NCL, bearing in mind that this Cys could be converted to Ala using the desulfurization reaction. To achieve the desired C-terminal functionality, peptide 1 is equipped with N-methylcysteine, as the N—S acyl transfer device (latent thioester functionality), in which the thiol side chain is protected with a photolabile-protecting group (2-nitrobenzyl) to avoid intramolecular N—S acyl transfer in the TFA-cleavage step. Upon completion of the ligation reaction, the thiol-protecting group is removed by UV, followed by activation of the fully unprotected polypeptide under acidic conditions, and treatment with MPA to afford the Ub-SR.

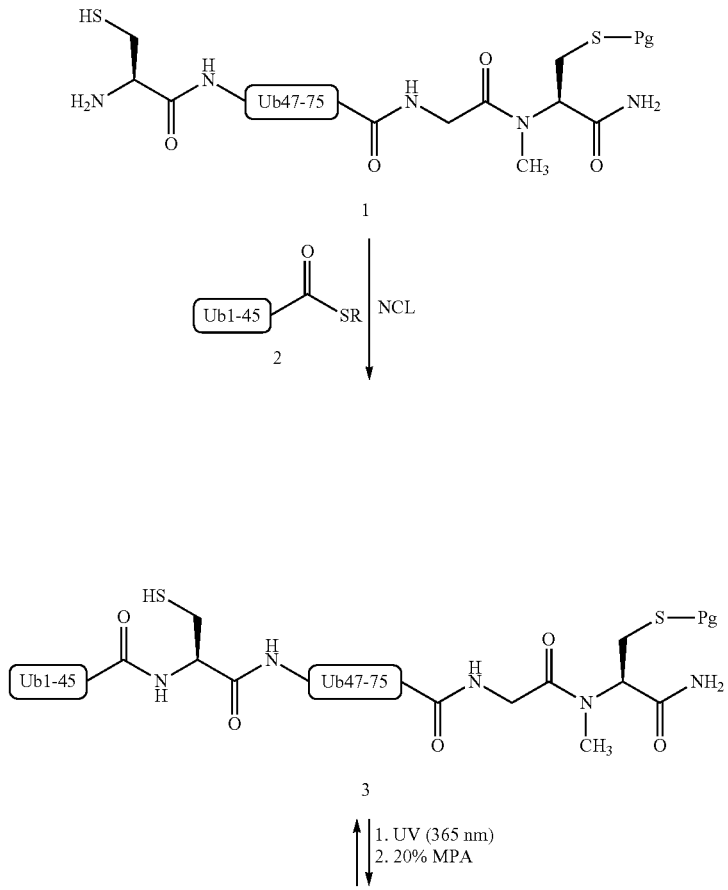

Scheme 3

-continued

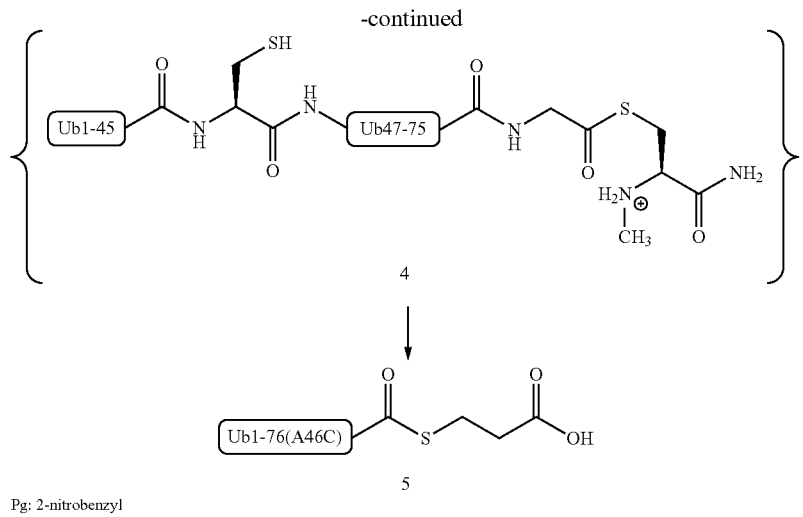

Pg: 2-nitrobenzyl

Thus, according to another aspect of the invention, there is provided a process for the preparation of ubiquitin thioesters, this process comprising:

a) Chemically synthesizing a first ubiquitin polypeptide fragment, being attached to a Latent Thioester Functionality (LTF) on the C-terminal of the ubiquitin fragment, further wherein this ubiquitin fragment contains an unprotected Cysteine amino acid on the N-terminal side thereof;

b) Chemically synthesizing a second ubiquitin fragment being complimentary to the first ubiquitin fragment obtained in step a, wherein this second ubiquitin is in a thioester form;

c) Ligating the first ubiquitin fragment with the second ubiquitin fragment, to obtain an unprotected ubiquitin polypeptide attached to the latent Thioester Functionality;

d) Reacting the ubiquitin polypeptide attached to the latent Thioester Functionality with an external thiol under acidic conditions to obtain the Ubiquitin thioester;

Optionally, the process described herein further comprises desulfurization of the Ubiquitin thioester to turn the unnatural Cys amino acid into an Ala amino acid, either before or after step (d).

Following this successful process, kits and apparatus for assembling polypeptide thioesters by the processes described herein are also provided.

Therefore, according to yet another aspect of the invention, there is provided a kit for preparing assembled polypeptide thioesters comprising:

(a) a latent thioester functionality, as described hereinabove, attached to the C-terminus of a first polypeptide or a fragment thereof, this fragment having a Cys residue at its N-terminus;

(b) optionally (if container (a) has only a fragment of the desired polypeptide), a second container containing a second polypeptide fragment having at its N-terminus a thioester; wherein the N-terminal cysteine of the first polypeptide fragment attached to the latent thioester functionality, is capable of selectively ligating to the N-terminus of the second polypeptide fragment, to form a polypeptide comprising the latent thioester functionality at its C-terminus; and (c) one or more additional containers containing an activating acid and an external thiol, capable of reacting with the polypeptide comprising a latent thioester functionality at its C-terminus, to provide a polypeptide thioester, wherein the acid and the thiol may be the same compound, or if different, may be provided either separately or in the same container.

Additional additives may be added to each of these container, or provided separately, in order to facilitate the ligation, the activation of the LTF group, or the obtaining of the final Ub thioester.

Preferably, the polypeptide thioester prepared using this kit is a ubiquitin thioester.

Preferably, the solid support is a bead resin.

Preferably, the Ub polypeptides or fragments thereof are all prepared by Solid phase peptide synthesis (SPPS).

According to a preferred embodiment, at least one of either polypeptide fragment (a), polypeptide fragment (b) or the complete polypeptide comprising the kit, contains an unnatural amino acid.

Preferably the unnatural amino acid is a 1,2 thioamine containing amino acid.

The term "1,2 thioamine containing amino acid" refers to amino acids containing the 1,2 thioamine group. Examples of 1,2 thioamine containing amino acids include, but are not limited to, mercaptolysine and various modifications thereof, as well as to the products obtained from the reaction of Cys amino acid with one of the following: glutamic acid, aspartic acid, Ser, Thr and Lys.

Preferably, the 1,2 thioamine containing amino acid is a protected mercaptolysine. Most preferably, the protected mercaptolysine is thiazolidine (Thz)-protected mercaptolysine.

The preparation of peptide fragment 1 was accomplished according to the sequence of reactions shown in Scheme 4 and detailed in Example 1.

Initially, the latent thioester functionality is attached to the solid support.

It is important to note that the attachment of the Latent Thioester Functionality (LTF) to the solid support may be conducted in one or several steps. For example, as shown in Scheme 4 and detailed in Example 1, a Rink amide resin was loaded with Fmoc-cys(2-nitrobenzyl)-OH using HBTU/DIEA coupling conditions. Subsequently, the Fmoc-protecting group was removed with 20% piperidine followed by coupling of the free amine with o-nitrobenzenesulfonyl chloride (o-NBS) to facilitate N-methylation. Selective deprotonation of the sulfonamide with DBU and alkylation with methyl p-nitrobenzenesulfonate in DMF led to the formation of the methylated sulfonamide resin 6. Alternatively, it was found that TBAF/MeI could also serve as an excellent choice for the methylation step. Selective removal of the o-NBS was achieved by using mercaptoethanol and DBU in DMF to obtain the N-methyl-cysteine, acting as LTF according to the present invention, being attached to the solid support.

Subsequently, SPPS was conducted, from amino acid (G) to amino acid (C), to obtain the desired peptide, the C-terminal of which being attached to the N-methyl-cysteine LTF, which is on its other side attached to the solid support throughout the SPPS. Side chain deprotection and release from the solid support using TFA/TIS/H$_2$O (95:2.5:2.5) afforded, after RP-HPLC purification, the desired peptide (Cys-Ub(47-76)-N-methyl Cysteine) in 25-30% isolated yield, whereas the obtained peptide has an unprotected Cys amino acid on its N-terminal, still attached to the LTF group on its C-terminal side, quite unlike common linkers in SPPS, which are usually detached either when the peptide is released from the resin, or during ligation under ligation conditions.

Pg: 2-nitrobenzyl

In one additional embodiments, this synthesis was continued in full to obtain the entire Ub polypeptide by SPPS, with the modification that the thiol protecting group on the LTF was trityl. In another embodiment, the full synthesis was repeated, while replacing the K amino acid at position 48 with a Thz-protected mercaptolysine. In both cases, final release from the solid support using TFA/TIS/H$_2$O (95:2.5:2.5), followed by reaction with MPA at a pH ranging from 1 to 2.

For the synthesis of Ub polypeptide fragment 2 (as it appears in Scheme 3) Ub(1-45)-SR, (R═—CH$_2$CH$_2$—COOMe), it was chosen to apply the N-acylurea chemistry, as is shown in Scheme 5 below and as detailed in Example 2.

Scheme 4

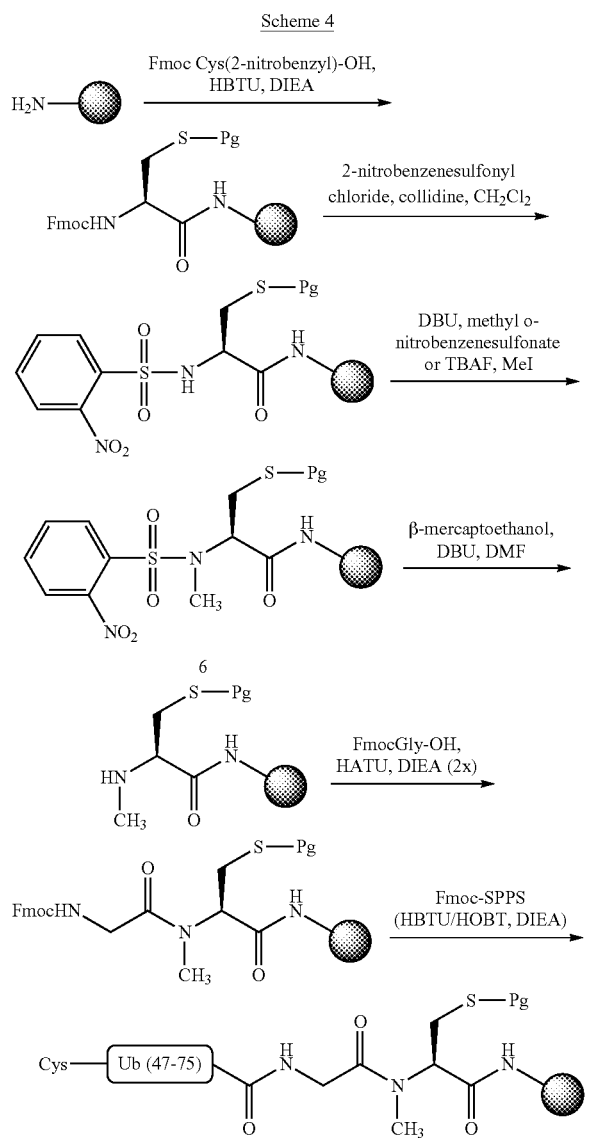

Scheme 5

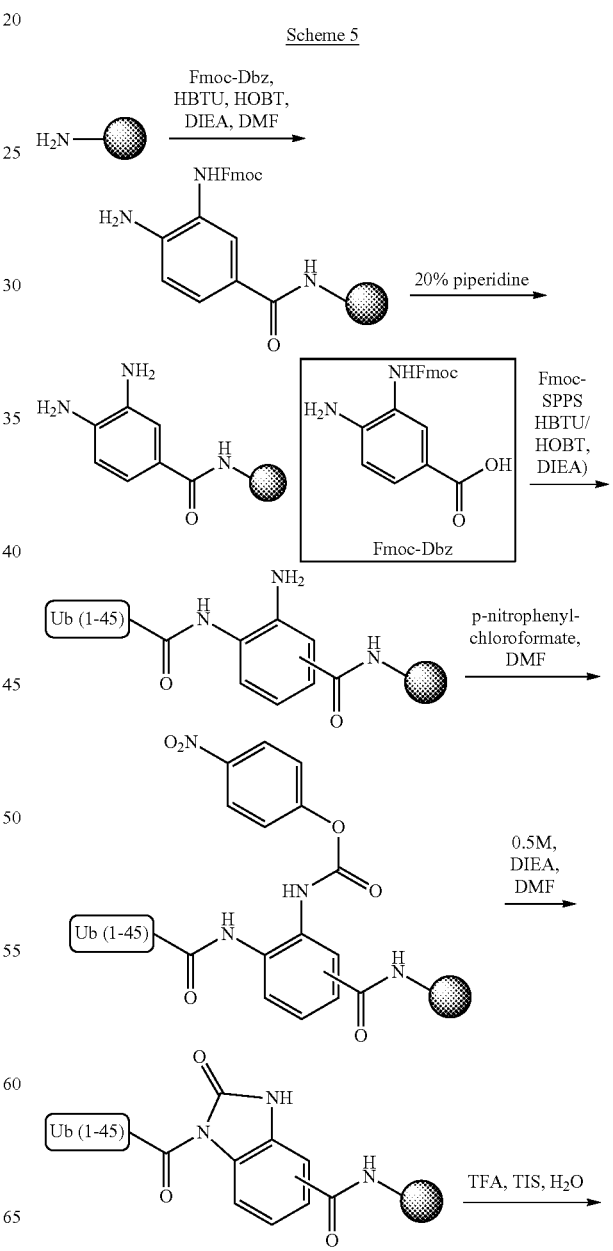

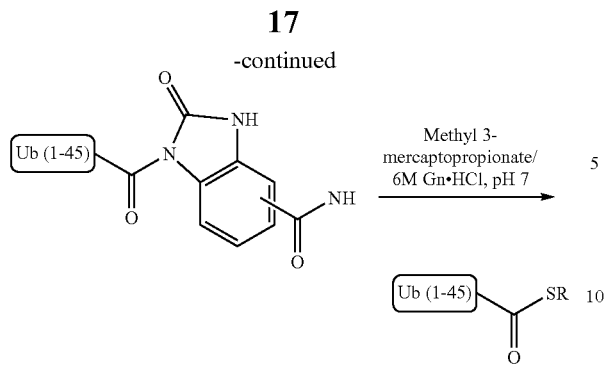

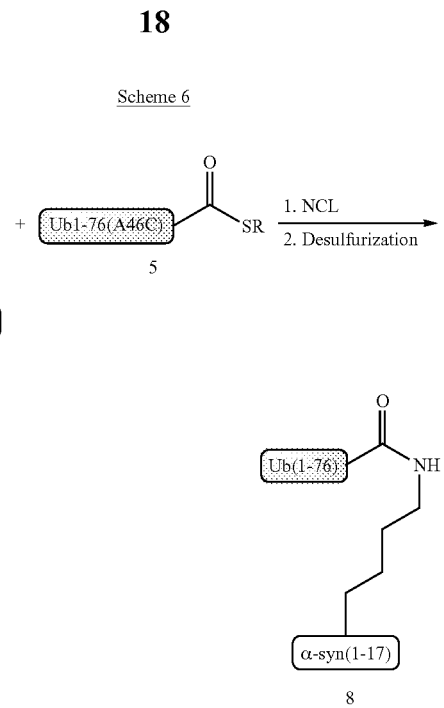

Scheme 6

As can be seen in Scheme 5 and in Example 2, SPPS was conducted using HBTU/DIEA coupling conditions on a rink resin, whereas the first amino acid being 3-Fmoc-4-damino benzoic acid (Fmoc-Dbz), a residue necessary for subsequent thioester formation, followed by Phe as the first Ub peptide fragment residue, and the last amino acid being coupled in the Boc protected form. On resin activation was conducted by adding p-nitrophenylchloroformate. The resin was washed with $CH_2Cl_2$ adding DIEA in DMF to obtain the peptide with the N-acyl benzimidazolinone functionality. This peptide was deprotected and cleaved from the resin by treatment with a mixture of $TFA/H_2O/TIS$ (95:2.5:2.5). After the lyophilization step, the crude peptide was treated with methyl 3-mercaptopropionate in 6M Gn.HCl, pH 7 to afford the Ub(1-45)-SR 2, after RP-HPLC purification step, in 20% yield.

As shown in Scheme 3, and as detailed in Example 3, the ligation between Ub peptide fragments 1 and 2 was carried out under NCL conditions i.e. 6 M Gn.HCl, 200 mM phosphate buffer, pH 7.5 in the presence of 2% (v/v) thiophenol/benzyl mercaptan. The reaction was followed by HPLC and mass spectrometry, which indicated nearly a complete ligation after 8 hours. As detailed in Example 4, following purification and lyophilization steps, when the thiol was protected by a photo-labile protecting group, the product was first exposed to UV light (365 nm) for 2 hours. The final step was the addition of 20% (v/v) MPA at at pH 2 and the reaction mixture was left at 37° C. After hours a full conversion to the desired thioester product was achieved. Preparative RP-HPLC purification and lyophilization afforded the Ub-SR in 30% isolated yield (for two steps).

To give further support of the integrity of the C-terminal thioester functionality, the synthetic Ub-SR was tested, as detailed in Example 5, in peptide ubiquitylation using α-synuclein(1-17) model peptide bearing the mercaptolysine residue. The results show that the synthetic Ub-SR is indeed an excellent substrate in the ligation reaction wherein within 4 hours a complete reaction was observed to afford the ubiquitylated peptide in 60% isolated yield. Furthermore, the ligation product was desulfurized using metal free desulfurization conditions to convert the Cys to Ala along with the full removal of the thiol handle from the mercaptolysine to furnish the ubiquitylated peptide 8 (Scheme 6). The desulfurized product was isolated in 75% yield and was treated with ubiquitin C-terminal hydrolase, UCH-L3 for 12 hours. The results show that the desulfurized product is indeed UCH-L3 substrate affording both the hydrolyzed Ub and the α-syn(1-17). Thus, the inventors have been able to show that the synthetic Ub-SR is in analogy to the E1-E2 activation steps and when combined with the ubiquitylation step using mercaptolysine, which resemble the E3 ligase activity, shows that the entire ubiquitylation process could be mimicked using chemical tools only.

Thus, the inventors have successfully proved that Ub-thioesters can be chemically synthesized, and have the same biological activity as the natural Ub-thioesters.

Furthermore, the authors have previously reported a new method for highly efficient and chemoselective peptide ubiquitylation utilizing δ-mercaptolysine residue, and have suggested that isopeptide formation assisted by δ-mercaptolysine is reminiscent to amide bond formation via NCL, which includes a capture step of the ubiquitin thioester (Ub-SR) to form a transient thioester intermediate that spontaneously rearranges through S—N acyl transfer step to form the isopeptide bond. To enable the incorporation of the δ-mercaptolysine residue, without it being unmasked during ligation or during Boc- or Fmoc-SPPS, the authors realized that protecting group variations of this residue are required. As can be seen below, the authors have now successfully devised a general strategy for the synthesis of different analogues of the δ-mercaptolysine (for example, compounds 1b-e, Scheme 7, vs. unprotected δ-mercaptolysine, 1a in this Scheme) bearing a variety of protecting groups on the α- and ε-amine, as well as on the δ-thiol paving the way for the use of these analogues in the synthesis of ubiquitylated proteins.

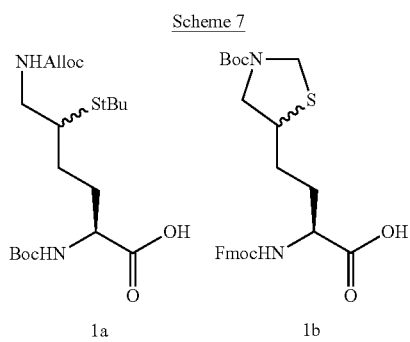

Scheme 7

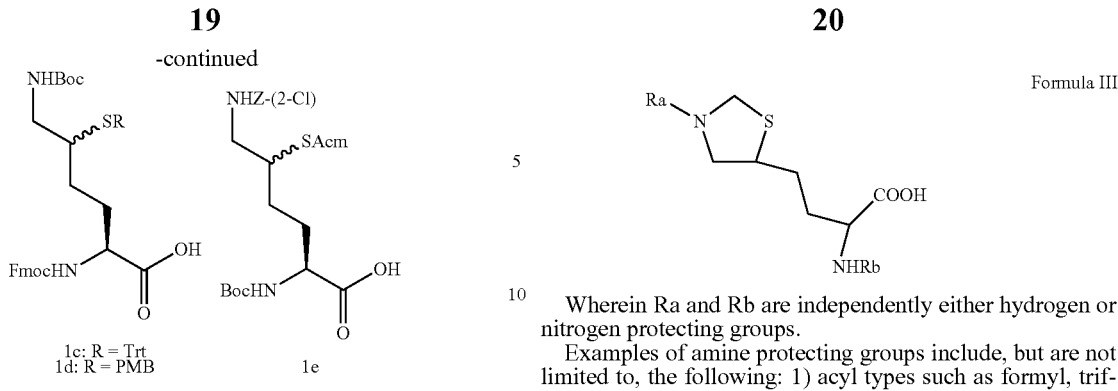

1c: R = Trt
1d: R = PMB

1e

While mercaptolysine derivative 1a could be incorporated in peptides and peptide thioesters using Boc-SPPS, after the removal of alloc under palladium catalysed reaction condition, treatment with HF or TFMSA would release all protecting groups from the mercaptoamine moiety. On the other hand, 1e under similar cleavage conditions (i.e., HF/TFMSA) would retain the mercapto functionality protected, thus making it useful in sequential ligation. Mercaptolysine derivatives 1b-d could be installed in peptides using Fmoc-SPPS. Again, while 1c, the equivalent to 1a, is completely unmasked under the cleavage conditions, 1b and 1d could be used in sequential ligation due to the orthogonality of the protecting groups (i.e., thiazolidine (Thz) and P-hydroxymercuribenzoate (PMB)).

Of particular interest is the thiazolidine (Thz)-protected mercaptolysine amino acid 1b, which can be easily turned into nucleophilic amine upon reaction with methoxylamine under acidic pH (of about 4).

This amino acid can be incorporated as a building-block in the structure of ubiquitin or other polypeptides, by replacing the similarly-structured Lys amino acid during SPPS of one or more fragments, as described herein. When this replacement is done during the preparation of a ubiquitin thioester, according to the present invention, there is obtained a ubiquitin thioester containing a protected mercaptolysine "handle", which can then be used in a variety of applications, such as sequential ligation, for example for preparing polyubiquitin chains, as disclosed in a patent application being co-filed on the same date as the instant application, having the reference number 11-069PCT, claiming the same priority (provisional application No. 61/302,359) and entitled "Chemical Preparation Of Polyubiquitin Chains", which is incorporated by reference as if fully set forth herein.

Thus, according to another aspect of the invention, there is provided a thiazolidine (Thz)-protected mercaptolysine amino acid.

According to a preferred embodiment, this amino acid serves as a building block for the ubiquitin thioester described hereinabove.

The term "building-block" as used herein refers to an amino acid which is incorporated in the sequence of the desired polypeptide, or polypeptide thioester, for example an amino acid which is incorporated in the sequence of the desired ubiquitin thioester, according to the present invention. The building block can be incorporated both on the main backbone of the polypeptide, as well as on a side chain thereof.

Preferably, the thiazolidine (Thz)-protected mercaptolysine amino acid described herein has the general formula III:

Formula III $$\text{Ra-N} \underset{\text{NHRb}}{\overset{\text{S}}{\bigtriangleup}} \text{—COOH}$$

Wherein Ra and Rb are independently either hydrogen or nitrogen protecting groups.

Examples of amine protecting groups include, but are not limited to, the following: 1) acyl types such as formyl, trifluoroacetyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boa), di-tert-butyl dicarbonate (Boc), ethoxycarbonyl, diisopropylmethoxycarbonyl, and allyloxycarbonyl; and 4) cyclic alkyl carbamate types such as cyclopentyloxycarbonyl and adamantyloxycarbonyl. Other Amine protecting groups are known to a person skilled in the art.

Preferably, Ra and Rb are either hydrogen or the protecting groups Boc or Fmoc.

The 1,2 thioamine containing amino acids disclosed hereinabove were prepared by first using nitro olefin 2 as the crucial building block, which allows the incorporation of the thiol functionality through 1,2-addition reaction at a high efficiency, as seen in Scheme 8 below. The obtained precursor 3b was used for the synthesis of other analogues bearing different protecting groups on the thiol functionality through the use of various thiol nucleophiles (Scheme XX).

Scheme 8

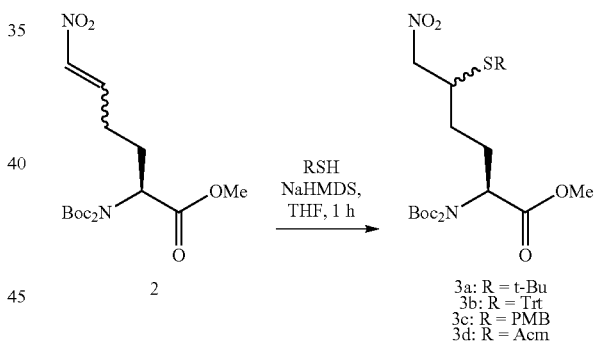

2

3a: R = t-Bu
3b: R = Trt
3c: R = PMB
3d: R = Acm

Thus, the 1,2-addition of trityl thiol, PMB-SH, acetamido methyl thiol and t-BuSH on 2 under NaHMDS/n-BuLi conditions furnished 3a-d in 75-85% yield. It should be noted that these reactions occurred in non-stereoselective fashion resulting in both isomers in a nearly equal ratio. However, the desulfurization reaction, which follows the ligation step, removes this diastereomeric center affording only single peptidic isomer.

In designing the synthesis of 1b-c, it was established that the synthesis of these analogues could be accomplished from the common intermediate 4 which can be obtained from 3b by replacing the di-boc to Fmoc protection (Scheme 3). Precursor 4 was converted to 5 through sequence of reactions, which included reduction of the nitro group using Zn/HCl, deprotection of the trityl group, incorporation of thiazolidine, and N-Boc protection. Subsequent hydrolysis of the methyl ester 5 yielded the target molecule 1b in 84% yield (FIG. 4). For the synthesis of 1c, intermediate 4 was initially subjected to a saponification step to give the acid derivative 6, that on reduction of the nitro group and N-Boc protection afforded the desired amino acid 1c (Scheme Scheme 9

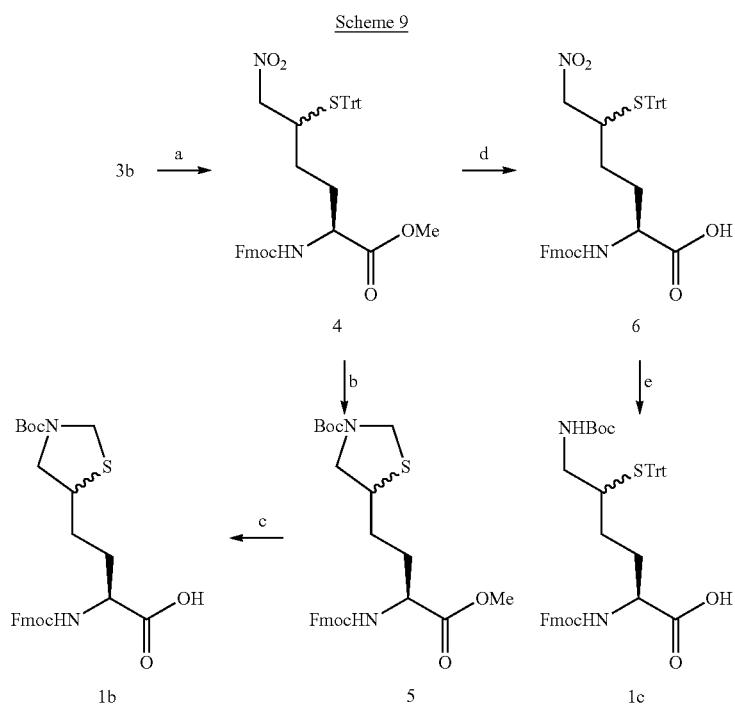

Whereas:

step a includes i) HCl(g), ethylacetate(dry), −20° C., 1 hour, and
ii) Fmoc-OSu, NaHCO₃, Dioxane-water, RT, 2 hours;
Step b includes:
i) Zn (dust), 10% HCl, 2 hours, RT;
ii) TFA, TIS, CH₂Cl₂, RT, 30 minutes,
iii) HCHO, NaHCO₃, MeOH, rt, 15 hours, and
iv) (Boc)₂O, RT, 15 hours;
Step c includes:
i) LiOH, THF—H₂O (4:2), 0° C., 1 hour,
Step d includes
i) LiOH, THF—H₂O (4:1), 0° C., 50 minutes; and
Step e includes:
i) Zn (dust), 10% HCl, 2 hours, RT; and
ii) (Boc)₂O, MeOH-TEA (10:1), 2 hours.

The conjugate addition product 3c was used for the synthesis of mercaptolysine analogue 1d in 5 steps process wherein the di-boc protecting group was first replaced with the Fmoc to yield precursor 7. The latter was reduced using NiCl₂/NaBH₄ conditions followed by protection using Boc-anhydride to give 8, which was subjected to a saponification step to afford the desired analogue 1d (Scheme 4). For the synthesis of 1e, the nitro group in 3d was reduced to the amine under NiCl₂/NaBH₄ conditions followed by protection with Z-(2-Cl)—OSu to give 9. Subsequently, the di-boc was switched to the mono-boc to afford 10, which was hydrolyzed to the target molecule 1e (Scheme 10).

Scheme 10

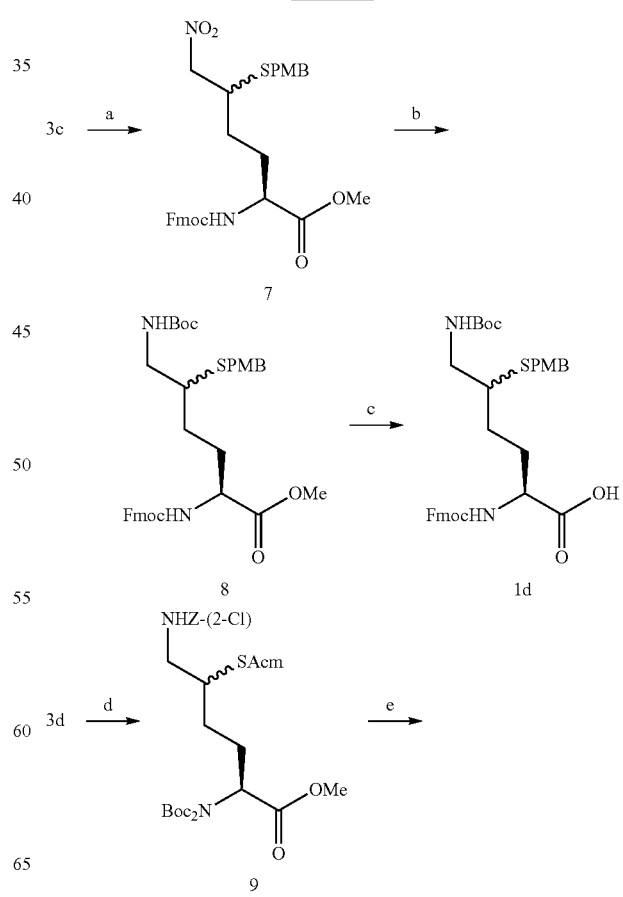

-continued

[Structures: Compound 10 (BocHN, OMe ester, SAcm, NHZ-(2-Cl)) → step f → Compound 1e (BocHN, OH, SAcm, NHZ-(2-Cl))]

Step a includes:
i) HCl(g), ethylacetate(dry), −20° C., 1 hour, and
ii) Fmoc-OSu, NaHCO$_3$, Dioxane-water, RT, 2 hours;
Step b includes:
i) NaBH$_4$, NiCl$_2$.6H$_2$O, THF-MeOH (1:1), −20 to −15° C., 35 minutes, and
ii) (Boc)$_2$O, MeOH-TEA (10:1), 2 hours;
Step c includes:
i) LiOH, THF—H$_2$O (4:2), 0° C., 1 hour;
Step d includes:
i) NaBH$_4$, NiCl$_2$.6H$_2$O, THF-MeOH (1:1), −20 to −15° C., 20 minutes,
ii) Z-(2-Cl)—OSu, NaHCO$_3$, Dioxane-water, RT, 2 hours;
Step e includes:
i) HCl(g), ethylacetate(dry), −20° C., 1 hour,
ii) (Boc)$_2$O, MeOH-TEA (10:1), 2 hours;
Step f includes:
i) LiOH, THF—H$_2$O (4:2), 0° C., 1 hour.

As explained hereinabove, the 1,2 thioamine substituents on Ub thioesters are important as sources for nucleophilic handles in reactions using the Ub thioesters. Therefore, according to a preferred embodiment of the invention, the ubiquitin thioesters described herein further contain at least one 1,2 thioamine containing amino acid.

Preferably, this 1,2 thioamine containing amino acid is a protected mercaptolysine. Most preferably, this protected mercaptolysine is thiazolidine (Thz)-protected mercaptolysine.

As seen in Example 7, the processes described in Examples 1-4 were repeated, with the only modification being the usage of unnatural amino acids (in this example 1,2 thioamine containing amino acid) in various stages of the process, instead of one of the seven natural lysines in ubiquitin (their natural positions being K6, K11, K27, K29, K33, K48, K63).

In particular, if the amino acid to be replaced is the Lys in positions 48 or 63, the modification is done during the preparation of fragment LTF-UbC, according to Example 1, by replacing the requested lysine by the 1,2 thioamine containing amino acid.

On the other hand, if the amino acid to be replaced is the Lys in positions 6, 11, 27, 29 or 33, the modification is done during the preparation of fragment UbN-SR, according to Example 2, by replacing the requested lysine by the 1,2 thioamine containing amino acid.

Therefore, according to yet another aspect of the present invention, there is provided a ubiquitin thioester comprising at least one ubiquitin monomer, this ubiquitin thioester containing at least one 1,2 thioamine containing amino acid. Preferably, the 1,2 thioamine containing amino acid is a protected mercaptolysine. Most preferably, the protected mercaptolysine is thiazolidine (Thz)-protected mercaptolysine.

According to additional preferred embodiments of the present invention, the Ubiquitin thioester described herein has the general formula II:

Formula II

[Structure: Ub$_m$–A$_p$–C(=O)–S–R]

wherein Ubm is a ubiquitin chain having m ubiquitin monomers, m being an integer equal to or larger than 1, R being selected from either alkyls or aryls, said alkyls or aryls being optionally substituted, and Ap being said 1,2 thioamine containing amino acid.

The term Ub chain as used herein refers to both mono-Ub and poly-Ub, namely ubiquitins having 1 or more monomers, as those have been defined hereinabove.

Preferably, the 1,2 thioamine containing amino acid is a protected mercaptolysine. Most preferably, the protected mercaptolysine is thiazolidine (Thz)-protected mercaptolysine.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Analytical Methods

Materials:
The meaning of the abbreviations used in the description and the claims is as outlined in the table below:
Fmoc 9-Fluorenylmethoxycarbonyl-
Boc t-Butoxycarbonyl-
DIEA Diisopropylethylamine
TFA Trifluoraceticacid
DMF N,N'-Dimethylformamide
HBTU O-Benzotriazole N,N,N',N'-tetramthyl-uronium-
HOBt 1-Hydroxybenzotriazole
DBU 1,8-Diazabicyclo[5.4.0]undec-7-ene
HATU O-(7-Azabenzotriazol-1-yl)-N,N,N',N'-tetramethyluronium-hexafluoro-phosphate
MEI Methyl iodide
TBAF Tetrabutylammonium Fluoride
MPA 3-mercaptopropionic acid
DTT Dithiothreitol
Tris Tris-(hydroxymethyl)aminomethane
THF Tetrahydrofuran
NaHMDS Sodium Hexamethyldisilazane
TIS Triisopropylsilane DMF was purchased in biotech grade. Commercial reagents were used without further purification.

Resins, protected and unprotected amino acids, and coupling reagents (HBTU, HOBt) were purchased from Novabiochem.

Buffer B is acetonitrile with 0.1% v/v TFA and buffer A is water with 0.1% v/v TFA.

Methanol, triethylamine, THF, ether were purified and dried before use.

The n-hexane used was the fraction distilling between 40-60° C.

Natural ubiquitin, which was used for comparison (from bovine erythrocytes) was purchased from Sigma.

All other chemicals were purchased from either Aldrich and/or Fluka.

SPPS was carried out manually in syringes, equipped with teflon filters, purchased from Torviq or by using an automated peptide synthesizer (CS336X, CSBIO). If not differently described, all reactions were carried out at room temperature. Note: Throughout this specification amino acid residues will be denoted by the three-letter abbreviation or single-letter code as follows:

| Three-letter | One-letter | Amino Acid abbreviation Symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Instrumental Data:

Mass spectrometry was conducted using LCQ Fleet Ion Trap (Thermo Scientific).

Analytical RP-HPLC was performed on a Thermo instrument (Spectra System p4000) using an analytical column (Jupiter 5 micron, C18, 300A 150×4.6 mm) and a flow rate of 1.2 ml/minute.

Preparative RP-HPLC was performed on an ECOM instrument using a preparative column (Jupiter 5 micron, C18, 300A, 250×10 mm) and a flow rate of 25 mL/minute.

Example 1

Preparation of N-methylcysteine Peptide Fragment 1 Ub(46-76) (LTF-UbC Fragment)

This example corresponds to Scheme 4.

In order to prepare a ubiquitin fragment containing a latent-Thioester-Functionality (LTF), a photolabile protected N-methyl-cysteine was first attached to the solid substrate as follows: Cys(2-nitrobenzyl)-OH was coupled to Rink amide resin (0.56 mmol/g; 0.1 mmol scale) using HBTU in 5 fold excess of the initial loading of the resin and DIEA was used in 10 fold excess. Peptide coupling was performed for 30 minutes. Fmoc deprotection was achieved by treatment of the resin with 20% piperidine.

Sulfonylation:

Collidine (264 µL, 20 eq) was dissolved in 1.5 mL of $CH_2Cl_2$ and added to the resin, followed by the addition of solution of o-nitrobenzenesulfonyl chloride (442 mgrams, 20 eq) in 1.5 mL of $CH_2Cl_2$. The resin was shaken for 2 hours at RT and was washed using $CH_2Cl_2$ (3×5 mL), and DMF (3×5 mL).

Alkylation:

To the washed resin from previous step, DBU (74 µL, 5 eq) in 1.5 mL of DMF was added followed by the addition of methyl 4-nitrobenzenesulfonate (108 mgrams, 5 eq) in 1.5 mL of DMF. The resin was shaken for 1 hour at RT and was washed using DMF (3×5 mL). Alternatively, MeI (124 µL, 20 eq) in 1 ml TBAF was added to the resin and was shaken for 0.1 hour.

Removal of NBS:

To a suspension of previously treated resin, DBU (38 µL, 5 eq) and mercaptoethanol (35 µL, 10 eq) were added in DMF and shaken well for 30 minutes at RT followed by DMF wash (3×5 mL).

Solid Phase Protein Synthesis (SPPS):

The first amino acid (Gly) was coupled using HATU (4 eq) and DIEA (10 eq) for 45 minutes (2×). The remaining amino acids were coupled using peptide synthesizer.

Cleavage from the Resin:

A mixture of TFA, triisopropylsilane and water (95:2.5:2.5) was added to the dried peptide-resin and the reaction mixture was shaken for 2 hours at RT. The resin was removed by filtration and was washed with TFA (2×2 mL). To precipitate the peptide the combined filtrate was added drop-wise to 10 fold volume of cold ether, centrifugation, decanting of ether, followed by dissolution of residue in acetonitrile-water and HPLC purification afforded the corresponding peptide fragment 1 (according to Scheme 3) in 25-30% yield.

In another experiment, the synthesis was continued in full to obtain the entire Ub polypeptide by SPPS, with the modification that the thiol protecting group on the LTF was trityl. Final release from the solid support using TFA/TIS/$H_2O$ (95:2.5:2.5) afforded the corresponding full-Ub peptide in 80% crude yield and 20-30% pure yield.

Example 2

Preparation of Ub Fragment 2 as Thioester (UbN-SR Fragment)

This example corresponds to Scheme 5.

Rink amide resin (0.2 mmol/grams, 0.1 mmol scale) was used for the synthesis of UbN-SR. Amino acids and HOBT/HBTU were used in 4-fold excess of the initial loading of the resin. DIEA was used in 10 fold excess. Fmoc deprotection was achieved by treatment of the resin with 20% piperidine. The first two amino acids, (i.e. 3-Fmoc-4-damino benzoic acid (Fmoc-Dbz), and Phe), were each double coupled manually for 1 hour. The remaining amino acids were coupled using peptide synthesizer. The last amino acid was coupled in the Boc protected form.

On Resin Activation:

After peptide elongation the resin was washed with $CH_2Cl_2$ and a solution of p-nitrophenylchloroformate (100 mgrams, 5 eq) in 10 ml of $CH_2Cl_2$ was added and shaken for 1 hour at RT. The resin was washed with $CH_2Cl_2$ (3×5 mL), and DMF (3×5 mL). To the washed resin a solution of 0.5 M DIEA in DMF (5 mL) was added and shaken for additional 30 minutes. The resin was washed using DMF (3×5 mL).

Cleavage and Purification:

The procedure used for peptide 1 was followed.

Thioesterification:

The pure peptide was dissolved in 0.2 M phosphate buffer (pH 7.98) containing 6 M guanidine.HCl to a final concentration of ~1 mM, followed by the addition of 2% (v/v) methyl-mercaptopropionate. The solution was kept at RT for 1 hour and purified by preparative reverse-phase HPLC using a linear gradient of 10-60% B over 30 minutes (buffer A: 0.1%

TFA in water; buffer B: 0.1% TFA in acetonitrile) to afford the corresponding thioester 2 (numbering according to Scheme 3) in ~80% crude yield and 35% pure yield.

Example 3

Native Chemical Ligation of Cys-UbC-LTF (1) and UM-SR (2)

This example corresponds to Scheme 3.

The ligation of unprotected peptide segments was performed following a known procedure: 3.2 mg of UbC and 5 mg of UbN-SR (1.1 eq) were dissolved in 440 µL of 0.2 M phosphate buffer (pH 7.98) containing 6 M guanidine.HCl to a final concentration of 2 mM. 2% (v/v) thiophenol and benzylmercaptan (8.7 µL) were added, and the ligation reaction was performed in a heating block at 37° C. The reaction was monitored using reverse-phase HPLC analysis on a C4 column using a linear gradient (10-60% B) over 30 minutes and purified on preparative HPLC using the similar gradient to obtain the ligation product 3 in a 36% yield.

Example 4

Removal of Thiol Protecting Group from Ligation Product, and Treatment with an External Thiol This example corresponds to Scheme 3.

Peptide 3, obtained in Example 3, was dissolved in photolysis buffer containing 10 mM ascorbic acid; 10 mM semicarbazide and 10 mM MPA in 0.2 M phosphate buffer (pH 7.98)/6 M guanidine.HCl for a final concentration of ~1 mM. The mixture was irradiated with UV at 365 nm, 28° C. for 2 hours. Subsequently, 20% MPA was added and the reaction was left at 37° C. for 12 hours. After completion of thioester formation the Ub-SR was purified using preparative RP-HPLC on C4 column and a linear gradient of 10-60% B over 30 minutes. The fractions were analyzed by ESI-MS and the desired fractions were collected, lyophilized to afford ubiquitin thioester 5 in 30% yield.

Example 5

Ubiquitylation by the Synthesized Ub-SR (5) on α-Synuclein (1-17) Model Peptide

This example corresponds to Scheme 6.

Ub-SR was tested in peptide ubiquitylation using α-synuclein(1-17) model peptide, as detailed below:

The α-synuclein(1-17) model peptide (7) was prepared using Boc solid phase peptide synthesis.

Ligation of Peptide (7) with Ubiquitin Thioester (5):

Purified peptides 5, (1.60 mgrams, 1 eq) and 7 (1 mgrams, 3 eq) were dissolved in 100 µL of 6 M guanidine.HCl, 200 mM phosphate buffer pH 7.98 (Due to TFA salts, after cleavage the actual pH after mixing the peptide was ~7.0). To this solution 2 µL each of benzyl mercaptan and thiophenol were added and incubated for 5 hours at 37° C. The reaction was followed using analytical column and a gradient of 10-60% B over 30 minutes. For preparative HPLC a similar gradient was used to afford the ligation product 8 (according to numbering in Scheme 6) in ~60% yield (~1.0 mg).

Desulfurization:

The ubiquitylated peptide was dissolved in argon purged 6 M guanidine.HCl 0.2 M Phosphate buffer pH 7.98 to a concentration of 2 mM. To this solution, a 0.5 M solution of TCEP in argon purged guanidine.HCl phosphate buffer pH 7.98 and 10% (v/v) of t-BuSH and 0.1 M radical initiator VA-044 were added, sequentially. The mixture was left at 37° C. for 3 hours. The extent of reaction was analyzed using C-4 analytical RP-HPLC employing a gradient of 10-60% B over 30 minutes to yield 75% of pure desulfurized peptide 8.

Enzymatic Cleavage of Isopeptide

Purified peptide 8 was dissolved in 482 µL of assay buffer (50 mM Tris, 150 mM NaCl, 1 mM DTT, pH 7.5) to a final concentration of ~100 µM and reacted with recombinant human ubiquitin C-terminal hydrolase L3 (UCH-L3, Aldrich). 10 µg of UCH-L3 in 15.5 µL of assay buffer containing 50 mM Tris, 150 mM NaCl, 12 mM DTT, pH 8.0 was incubated for 20 minutes at 25° C. To the reduced UCH-L3 was then added 8 in 187 µL. The mixture was incubated for 12 hours at 37° C., at which a complete hydrolysis was achieved. The reaction was analyzed using C-4 analytical RP-HPLC employing a gradient of 10-60% B for 30 minutes, in order to identify the hydrolysis.

Example 6

Preparation of Thz-Protected Mercaptolysine

Thz-protected mercaptolysine was prepared by the following steps. The compound numbers correspond to the numbers on Schemes 7-10:

Preparation of Protected Amino Acid 3b:

This example corresponds to Scheme 8.

A 50 mL round-bottom flask equipped with argon inlet, a rubber septum, and a stirring bar, was charged with trityl thiol (2.19 mmol) in dry THF (10 mL), and cooled to −40° C. To this solution was added NaHMDS (0.6 M, 3.66 mL, 2.19 mmol), and stirred for 10 minutes. The reaction mixture was cooled to −78° C. and stirring was continued for additional 5 minutes. A solution of nitro olefin, 2 (1.83 mmol) in dry THF (15 mL) was then added over a period of 10 minutes. After 40 minutes of stirring, the reaction was quenched with saturated. aqueous solution of $NH_4Cl$ (5 mL), diluted with water (20 mL) and extracted with ethyl acetate (3×15 mL). The combined organic extracts were washed with brine (15 mL), dried over $Na_2SO_4$ and purified using flash column chromatography (silica gel, ethyl acetate/n-hexane) afforded ~1:1 diastereomeric mixture of Compound 3b in Yield: 1.08 grams (89%). Rf=0.51 (ethyl acetate/n-hexane 1/4)

Analysis of Compound 3:

$^1$H NMR (500 MHz, $CDCl_3$, 20° C., TMS): d 1.40 (s, 9H; —OC(CH$_3$)$_3$), 1.41 (9H; —OC(CH$_3$)$_3$), 1.53-1.69 (m, 2H; H-2), 1.79-1.87, 2.05-2.09, 2.17-2.24 (m, 2H; H-3), 2.92-2.96 (m, 1H; H-4), 3.10 and 3.17 (2×dd, J=3.9, 13.1 Hz, 1H; H-5a), 3.60, 3.63 (2×s, 3H; —OCH$_3$), 3.87 and 3.94 (2×dd, J=10.7, 13.3 Hz, 1H; H-5b), 4.66-4.71 (m, 1H; H-1), 7.14-7.17 (m, 3H; ArH), 7.20-7.24 (m, 6H; ArH), 7.42-7.46 (m, 6H; ArH);

$^{13}$C NMR (125 MHz, CDCl3, 20° C.): d 25.9 (C-2); 26.0 (2×—OC(CH$_3$)$_3$), 28.8 (C-3), 29.0 (C-4), 41.4 (—SC(Ph)$_3$), 52.2 (OCH$_3$), 57.6 (C-1), 77.4 (C-5), 83.3 (2×—OC(CH$_3$)$_3$), 127.0 (3×ArCH), 128.2 (6×ArCH), 129.2 (6×ArCH), 144.1 (3×ArC), 151.8 (2×—NC(O)OC(CH$_3$)$_3$), 170.8 (—C(O)OCH$_3$).

Preparation of Intermediate Nitro Compound 4 by Replacing the di-boc in the Protected Amino Acid 3 to Fmoc Protection:

This example corresponds to Scheme 9.

The protected amino acid 3b (1.08 grams, 1.62 mmol) was dissolved in dry ethyl acetate (25 mL) and cooled to −20° C. followed by purging with dry HCl(g). After 1 hour, the mixture was concentrated and dried to give the hydrochloride salt of the corresponding amine. The resulting amine hydrochloride was dissolved in Dioxane-Water (2:1) (6 mL) and aqueous sodium bicarbonate solution (4M, 6.47 mmol) was added, stirred for 5 minutes at RT. Fmoc-Osu (0.55 grams, 1.63 mmol) was dissolved in dioxane (3.5 mL) and added dropwise to the previous mixture. After 2 hours of stirring, the reaction mixture was poured into water and extracted using ethyl acetate (3×15 mL). The combined organic layers were dried ($Na_2SO_4$), concentrated and purified using flash column chromatography (silica gel, ethyl acetate/n-hexane 25/75) afforded 4 as a thick liquid (0.72 grams, 96% over two steps): $R_f$=0.56 (ethyl acetate/n-hexane 3/7).

Analysis of Compound 4:

$^1$H NMR (500 MHz, $CDCl_3$, 20° C., TMS): δ 1.47-1.72 (m, 2H; H-2), 1.77-1.84, 1.91-2.05 (m, 2H; H-3), 2.81-2.88 (m, 1H; H-4), 3.26 and 3.45 (2×dd, J=3.8, 13.1 and 3.9, 13.1 Hz, 1H; H-5a), 3.62 (s, 3H; O$CH_3$), 3.86-3.93 (m, 1H; H-5b), 4.11 (t, J=6.8 Hz, 1H; CH(Fmoc)), 4.20-4.23 (m, 1H; H-1), 4.27-4.30 (m, 2H; $CH_2$(Fmoc)), 5.15-5.18 (m, 1H; N$\underline{H}$), 7.09-7.13 (m, 3H; ArH), 7.16-7.27 (m, 8H; Fmoc), 7.25-7.32 (m, 2H; ArH), 7.41 (d, J=7.8 Hz, 6H; ArH), 7.49 (t, J=6.3 Hz, 2H; ArH), 7.63-7.67 (m, 2H; ArC);

$^{13}$C NMR (125 MHz, $CDCl_3$, 20° C.): δ 27.9 (C-2), 28.3 (C-3), 28.7 (—$\underline{C}$(Ph)$_3$), 41.2 (C-4), 47.0 (CH(Fmoc)), 52.4 (O$CH_3$), 53.4 (C-1), 67.0 ($CH_2$(Fmoc)), 77.3 (C-5), 119.9 (2×ArCH), 125.0 (2×ArCH), 127.0 (3×ArCH), 127.6 (2×ArCH), 128.2 (6×ArCH), 129.2 (6×ArCH), 141.2 (ArC), 143.7 (ArC), 143.9 (3×ArC), 155.7 (—NHC(O)O(Fmoc)), 172.2 (—$\underline{C}$(O)O$CH_3$).

ESI-MS: Calculated for $[C_{41}H_{38}N_2O_6S.Na^+]^+$: 709.8 Da, Observed: 709.3 Da.

Preparation of Intermediate Compound 5 by Reduction Of the Nitro Group, Deprotection of the Trityl Group, Incorporation of Thiazolidine, and N-Boc Protection of Intermediate Nitro Compound 4:

This example corresponds to Scheme 9.

To a stirred solution of nitro compound 4 (0.24 grams, 0.36 mmol) in methanol (14 mL) at room temperature was added Zn powder (0.47 grams, 7.11 mmol) followed by dropwise addition of 10% HCl solution (2.5 mL). The reaction was stirred at room temperature until starting material was consumed based on TLC. The reaction mixture was filtered through celite-545 bed, concentrated, and dried on high vacuum. The dried amine hydro chloride was treated with TFA-$CH_2Cl_2$ (1:1) (4 mL) and TIS (0.11 mL, 0.53 mmol) for 1 hour at room temperature, then concentrated, dried under high vacuum. The crude product was dissolved in MeOH-water (4:1) (5 mL), followed by the addition of sodium bicarbonate (0.03 grams, 0.36 mmol) and the mixture was stirred for 15 minutes. To this mixture, formaldehyde (37% in water) (0.03 mL, 0.39 mmol) was added and stirred for 15 hours at 25° C. Subsequently, $(Boc)_2O$ (0.09 grams, 0.43 mmol) was added and stirring was continued for additional 15 hours. The reaction mixture was concentrated and extracted using ethyl acetate (3×15 mL). The combined organic layers were dried, concentrated, and purified using flash column chromatography (silica gel, ethyl acetate/n-hexane 25/75) to afford 5 as a foamy white solid (0.076 grams, 40% over four steps).

Analysis of Compound 4:

$^1$H NMR (500 MHz, $CDCl_3$, 20° C., TMS): δ 1.47-1.48 (2×s, 9H; OC($CH_3$)$_3$), 1.60-1.80 (m, 3H; H-2, H-3a), 1.92-2.06 (m, 1H; H-3b), 3.39 (m, 2H; H-4, H-5a), 3.73-3.76 (m, 1H; H-5b), 3.74 (s, 3H; COO$CH_3$), 4.23 (t, J=6.9 Hz, 1H; CH(Fmoc)), 4.39-4.43 (m, 5H; H-1, H-6, $CH_2$(Fmoc)), 5.37 (d, J=8.2 Hz, 1H; N$\underline{H}$), 7.30-7.35 (m, 2H; ArH), 7.39-7.43 (m, 2H; ArH), 7.59-7.61 (m, 2H; ArH), 7.77-7.78 (m, 2H; ArH);

$^{13}$C NMR (125 MHz, $CDCl_3$, 20° C.): δ 28.3 (—C($\underline{CH_3}$)$_3$), 29.6 (C-2), 31.4 (C-3), 46.1 (C-4), 47.1 (CH-Fmoc), 48.0 (C-5), 52.5 (OMe), 53.7 (C-1), 54.0 (S$CH_2$N), 66.9 ($CH_2$(Fmoc)), 80.5 (O—$\underline{C}$($CH_3$)$_3$), 119.9 (2×ArC), 125.0 (2×ArC), 127.0 (2×ArC), 127.6 (2×ArC), 141.2 (2×ArC), 143.6 (2×ArC), 153.6 (—N(CO)OC($CH_3$)$_3$), 155.8 (NHC(O)O(Fmoc)), 172.5 (—$\underline{C}$(O)OMe).

ESI-MS: Calculated for $[C_{28}H_{34}N_2O_6S.Na^+]^+$: 549.6 Da, Observed: 549.3 Da.

Preparation of Protected Mercaptolysine 1b from Intermediate Compound 5:

This example corresponds to Scheme 9.

To an ice-cooled solution of 5 (0.076 grams, 0.14 mmol) in THF-water (4:1) (2.5 mL) 0.3 M solution of LiOH (0.018 grams, 0.43 mmol) in water was added in three portions over a period of 10 minutes After stirring at 0° C. for 1 hour, the pH of reaction mixture was adjusted to pH 3-4 using cold 10% (w/v) citric acid solution, and extracted with ethyl acetate (5×10 mL). The combined organic layers were dried, concentrated, and purified using flash column chromatography (silica gel, MeOH/$CHCl_3$ 3/7) to give 1b as a thick mass (0.061 grams, 84%): $R_f$=0.25 (MeOH/$CHCl_3$ 1/4).

Analysis of Compound 1b:

$^1$H NMR (500 MHz, $CDCl_3$, 20° C., TMS): δ 1.38-1.39 (2×s, 9H; OC($CH_3$)$_3$), 1.51-1.72 (m, 3H; H-2, H-3a), 1.87-1.98 (m, 1H; H-3b), 3.29-3.31 (m, 2H; H-5a, H-4), 3.57-3.67 (m, 1H; H-5b), 4.13 (t, J=6.7 Hz, 1H; CH(Fmoc)), 4.23-4.44 (m, 5H; H-1, S$CH_2$N, $CH_2$(Fmoc)), 5.48-5.57 (m, 1H; (exchangeable with $D_2$O)N$\underline{H}$), 6.01-6.21 (m, 1H; (exchangeable with $D_2$O), COO$\underline{H}$), 7.19-7.24 (m, 2H; ArH), 7.30 (t, J=7.4 Hz, 2H; ArH), 7.49-7.52 (m, 2H; ArH), 7.67 (d, J=7.5 Hz, 2H; ArH);

$^{13}$C NMR (125 MHz, $CDCl_3$, 20° C.) δ 28.3 (—C($\underline{CH_3}$)$_3$), 29.8 (C-2), 31.1 (C-3), 45.9 (C-4), 47.0 (CH(Fmoc)), 47.9 (C-5), 53.4 (C-1), 53.9 (S$CH_2$N), 67.0 (O$CH_2$(Fmoc)), 80.9 (O$\underline{C}$($CH_3$)$_3$), 119.9 (2×ArC), 125.0 (2×ArC), 127.0 (2×ArC), 127.7 (2×ArC), 141.2 (2×ArC), 143.7 (2×ArC), 153.9 (—NC(O)OC($CH_3$)$_3$), 156.1 (NHC(O)O(Fmoc)), 175.4 (—$\underline{C}$(O)OH).)

ESI-MS: Calculated for $[C_{27}H_{32}N_2O_6S.Na^+]^+$: 535.6. Observed: 535.3 Da.

Example 7

Preparation of Thioester Ub Containing a 1,2 thioamine Group (Modified Thioesters)

In one example, ubiquitin thioesters containing THZ-protected mercaptolysine, prepared according to Example 6, as an unnatural amino acid in position 48, instead of the natural Lys in that position, according to the process of Example 1. The subsequent stages (Examples 2, 3 and 4) were repeated in the same manner to obtain the product $Ub_{k48}$-thioester in 30% overall yield. The structure was confirmed by MS and HPLC.

In another example, the SPPS synthesis of fragment 1 (as in Example 1) was continued in full to obtain the entire Ub polypeptide by SPPS, with the modification that the thiol protecting group on the LTF was trityl and further by replacing the K amino acid at position 48 with a Thz-protected mercaptolysine, as prepared according to Example 6. The final release from the solid support was done using TFA/TIS/$H_2O$ (95:2.5:2.5), and was followed by reaction with MPA at a pH ranging from 1 to 2 to obtain the final product in a 20-30% pure yield. The structure was confirmed by MS and HPLC.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A modified ubiquitin polypeptide, or a modified fragment thereof, said polypeptide or fragment thereof comprising a ubiquitin polypeptide, or a fragment thereof, attached to a N—S acyl transfer device at the C-terminus of said ubiquitin or said fragment thereof, wherein said modified fragment is selected from CKIQDKEGIPPDQQRLIF (Ub28-45) (SEQ ID NO:10), CGKQLEDGRTLSDYNIQKESTLHLVLRLRGG (Ub46-76) (SEQ ID NO:8) and CKIQDKEGIPPDQQRLIFAGKQLEDGRTLSDYNIQKESTLHLVLRLRGG (Ub46-76) (SEQ ID NO:8) and CKIQDKEGIPPDQQRLIF-AGKQLEDGRTLSDYNIQKESTLHLVLRLRGG (Ub28-76) (SEQ ID NO:9);

and wherein said N—S acyl transfer device has the general Formula I:

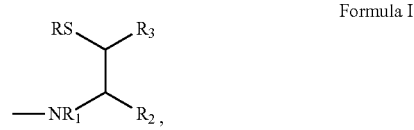

Formula I wherein
R=hydrogen or 2-nitrobenzyl; $R_1$=methyl; $R_2$=CONH$_2$; $R_3$=hydrogen.

2. The modified ubiquitin polypeptide or modified fragment thereof of claim 1, wherein said N—S acyl transfer device is linked at position 45 of said fragment or at position 76 of said ubiquitin or of said fragment thereof.

* * * * *

SEQUENCE LISTING

```
<160> NUMBER OF SEQ ID NOS: 10

<210> SEQ ID NO 1
<211> LENGTH: 76
<212> TYPE: PRT
<213> ORGANISM: Homo sapiens

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2
<211> LENGTH: 76
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthesized ubiquitin with the N-terrminus
      methionine replaced by leucine.

<400> SEQUENCE: 2

Leu Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 3
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic peptide intended for attchment at
      its C terminal to a latent thioester functionaly (LTF).
```

-continued

```
<400> SEQUENCE: 3

Ala Gly Lys Gln Leu Glu Asp Gly Arg Thr Leu Ser Asp Tyr Asn Ile
1               5                   10                  15

Gln Lys Glu Ser Thr Leu His Leu Val Leu Arg Leu Arg Gly Gly
            20                  25                  30

<210> SEQ ID NO 4
<211> LENGTH: 45
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Second fragment in thioester form, intended for
      native chemical ligation with Ub46-76

<400> SEQUENCE: 4

Leu Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe
        35                  40                  45

<210> SEQ ID NO 5
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic peptide attached at its C terminus
      to a latent thioester functionality (LTF).

<400> SEQUENCE: 5

Ala Lys Ile Gln Asp Lys Glu Gly Ile Pro Pro Asp Gln Gln Arg Leu
1               5                   10                  15

Ile Phe Ala Gly Lys Gln Leu Glu Asp Gly Arg Thr Leu Ser Asp Tyr
            20                  25                  30

Asn Ile Gln Lys Glu Ser Thr Leu His Leu Val Leu Arg Leu Arg Gly
        35                  40                  45

Gly

<210> SEQ ID NO 6
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Second synthetic peptide fragment in thioester
      form, intended for native chemical ligation with Ub28-76

<400> SEQUENCE: 6

Leu Gln Ile Phe Val Lys Thr Leu Thr Gly Lys Thr Ile Thr Leu Glu
1               5                   10                  15

Val Glu Pro Ser Asp Thr Ile Glu Asn Val Lys
            20                  25

<210> SEQ ID NO 7
<211> LENGTH: 18
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Third synthetic peptide ubiquitin fragment
      intended for native chemical ligation together with Ub46-76 and
      Ub1-27

<400> SEQUENCE: 7

Ala Lys Ile Gln Asp Lys Glu Gly Ile Pro Pro Asp Gln Gln Arg Leu
1               5                   10                  15

Ile Phe

<210> SEQ ID NO 8
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic peptide intended for attachment at
      its C terminal to a latent thioester functionality (LTF), with its
      N-terminal alanine replaced by cysteine.

<400> SEQUENCE: 8

Cys Gly Lys Gln Leu Glu Asp Gly Arg Thr Leu Ser Asp Tyr Asn Ile
1               5                   10                  15

Gln Lys Glu Ser Thr Leu His Leu Val Leu Arg Leu Arg Gly Gly
            20                  25                  30

<210> SEQ ID NO 9
<211> LENGTH: 49
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic peptide attached at its C terminus
      to a latent thioester functionality (LTF), with its N-terminal
      alanine replaced by cysteine.

<400> SEQUENCE: 9

Cys Lys Ile Gln Asp Lys Glu Gly Ile Pro Pro Asp Gln Gln Arg Leu
1               5                   10                  15

Ile Phe Ala Gly Lys Gln Leu Glu Asp Gly Arg Thr Leu Ser Asp Tyr
            20                  25                  30

Asn Ile Gln Lys Glu Ser Thr Leu His Leu Val Leu Arg Leu Arg Gly
        35                  40                  45

Gly

<210> SEQ ID NO 10
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Third synthetic peptide ubiquitin fragment
      intended for native chemical ligation together with Ub46-76 and
      Ub1-27, with its N-terminal alanine replaced by cysteine.
```

```
<400> SEQUENCE: 10

Cys Lys Ile Gln Asp Lys Glu Gly Ile Pro Pro Asp Gln Gln Arg Leu
1               5                   10                  15

Ile Phe
```